(12) United States Patent
Mohan et al.

(10) Patent No.: US 10,123,900 B2
(45) Date of Patent: Nov. 13, 2018

(54) DEVICES, KITS, AND METHODS FOR THE TREATMENT OF OBSTRUCTIVE SLEEP APNEA

(71) Applicants: Cook Biotech Incorporated, West Lafayette, IN (US); Cook Medical Technologies LLC, Bloomington, IN (US)

(72) Inventors: Arun Mohan, Lafayette, IN (US); Darin Schaeffer, Bloomington, IN (US); Christopher Nelson, Lafayette, IN (US); Patrick Melder, Marietta, GA (US); Dan Dalenberg, Portage, MI (US)

(73) Assignees: COOK MEDICAL TECHNOLOGIES LLC, Bloomington, IN (US); COOK BIOTECH INCORPORATED, West Lafayette, IN (US)

( * ) Notice: Subject to any disclaimer, the term of this patent is extended or adjusted under 35 U.S.C. 154(b) by 673 days.

(21) Appl. No.: 14/211,704

(22) Filed: Mar. 14, 2014

(65) Prior Publication Data

US 2014/0272781 A1    Sep. 18, 2014

Related U.S. Application Data

(60) Provisional application No. 61/793,343, filed on Mar. 15, 2013.

(51) Int. Cl.
  *A61C 1/08*    (2006.01)
  *A61F 5/56*    (2006.01)
  (Continued)

(52) U.S. Cl.
  CPC .............. *A61F 5/566* (2013.01); *A61B 13/00* (2013.01); *A61B 17/06109* (2013.01);
  (Continued)

(58) Field of Classification Search
  CPC ..................... A61C 1/082–1/085; A61F 5/566
  (Continued)

(56) References Cited

U.S. PATENT DOCUMENTS 3,414,975 A * 12/1968 Small ................... A61B 17/176
                                                    433/174
3,895,444 A *  7/1975 Small ..................... A61C 8/003
                                                    433/174
(Continued)

FOREIGN PATENT DOCUMENTS

WO    WO2007056583    5/2007
WO     2007149469    12/2007
(Continued)

OTHER PUBLICATIONS

European Patent Office. Extended European Search Report, for App. No. 14160336.5, dated Jun. 17, 2014. p. 1-4.
(Continued)

*Primary Examiner* — Matthew Nelson
(74) *Attorney, Agent, or Firm* — Buchanan Van Tuinen LLC

(57) ABSTRACT

Devices, kits, and methods useful in the treatment of Obstructive Sleep Apnea (OSA) are described. Example devices include a jig, a first needle, a second needle, and a third needle. An example jig comprises a drill guide and a tongue depressor. A first needle comprises an elongate shaft that defines a bend and a curve. A second needle comprises an elongate shaft that defines a curve. A third needle comprises an elongate shaft that defines a curve.

20 Claims, 10 Drawing Sheets

(51) Int. Cl.
   *A61B 13/00* (2006.01)
   *A61B 17/17* (2006.01)
   *A61B 17/06* (2006.01)
   *A61B 17/00* (2006.01)
   *A61B 17/24* (2006.01)
   *A61B 17/88* (2006.01)

(52) U.S. Cl.
   CPC ............ *A61B 17/176* (2013.01); *A61C 1/085* (2013.01); *A61B 17/8805* (2013.01); *A61B 17/8811* (2013.01); *A61B 2017/00814* (2013.01); *A61B 2017/06076* (2013.01); *A61B 2017/248* (2013.01)

(58) Field of Classification Search
   USPC .............................................. 433/72, 75, 76
   See application file for complete search history.

(56) References Cited

U.S. PATENT DOCUMENTS

| | | | |
|---|---|---|---|
| 4,024,859 A | | 5/1977 | Slepyan et al. |
| 4,064,873 A | | 12/1977 | Swenson |
| 4,364,381 A | * | 12/1982 | Sher .................... A61B 17/176 606/916 |
| 4,608,972 A | | 9/1986 | Small |
| 4,917,604 A | * | 4/1990 | Small .................... A61C 1/084 433/173 |
| 5,674,191 A | | 10/1997 | Edwards et al. |
| 5,688,283 A | * | 11/1997 | Knapp .................... A61C 1/084 433/75 |
| 5,988,171 A | * | 11/1999 | Sohn .................. A61B 17/0401 128/848 |
| 6,159,208 A | | 12/2000 | Hovda et al. |
| 6,408,851 B1 | | 6/2002 | Karell |
| 6,513,530 B2 | | 2/2003 | Knudson et al. |
| 6,513,531 B2 | | 2/2003 | Knudson et al. |
| 6,523,541 B2 | | 2/2003 | Knudson et al. |
| 6,955,172 B2 | | 10/2005 | Nelson et al. |
| 7,004,941 B2 | | 2/2006 | Tvinnereim et al. |
| 7,047,979 B2 | | 5/2006 | Conrad et al. |
| 7,063,089 B2 | | 6/2006 | Knudson et al. |
| 7,073,505 B2 | | 7/2006 | Nelson et al. |
| 7,090,672 B2 | | 8/2006 | Underwood et al. |
| 7,101,181 B2 | * | 9/2006 | Bompard ............... A61C 1/084 433/75 |
| 7,188,627 B2 | | 3/2007 | Nelson et al. |
| 7,213,599 B2 | | 5/2007 | Conrad et al. |
| 7,255,109 B2 | | 8/2007 | Knudson et al. |
| 7,337,781 B2 | | 3/2008 | Vassallo |
| 7,360,542 B2 | | 4/2008 | Nelson et al. |
| 7,363,926 B2 | | 4/2008 | Pflueger et al. |
| 7,387,634 B2 | | 6/2008 | Benderev |
| 7,401,611 B2 | | 7/2008 | Conrad et al. |
| 7,491,200 B2 | | 2/2009 | Underwood |
| 7,607,439 B2 | | 10/2009 | Li |
| 7,644,714 B2 | | 1/2010 | Atkinson et al. |
| 7,658,192 B2 | | 2/2010 | Harrington |
| 7,669,603 B2 | | 3/2010 | Knudson et al. |
| 7,673,635 B2 | | 3/2010 | Conrad et al. |
| 7,680,538 B2 | | 3/2010 | Durand et al. |
| 7,703,460 B2 | | 4/2010 | Conrad et al. |
| 7,766,926 B2 | | 8/2010 | Bosley, Jr. et al. |
| 7,845,357 B2 | | 12/2010 | Buscemi et al. |
| 7,909,037 B2 | | 3/2011 | Hegde et al. |
| 7,909,038 B2 | | 3/2011 | Hegde et al. |
| 7,921,850 B2 | | 4/2011 | Nelson et al. |
| 7,934,506 B2 | | 5/2011 | Woodson et al. |
| 7,954,494 B1 | | 6/2011 | Connor |
| 7,959,554 B2 | | 6/2011 | McAlexander et al. |
| 7,975,700 B2 | | 7/2011 | Frazier et al. |
| 7,980,248 B2 | | 7/2011 | Hegde et al. |
| 7,992,564 B2 | | 8/2011 | Doshi et al. |
| 7,992,566 B2 | | 8/2011 | Pflueger et al. |
| 7,992,567 B2 | | 8/2011 | Hirotsuka et al. |
| 7,997,266 B2 | | 8/2011 | Frazier et al. |
| 8,074,655 B2 | | 12/2011 | Sanders |
| 8,096,303 B2 | | 1/2012 | Dineen et al. |
| 8,167,787 B2 | | 5/2012 | Gillis |
| 8,220,466 B2 | | 7/2012 | Frazier et al. |
| 8,220,467 B2 | | 7/2012 | Sanders |
| 8,327,854 B2 | | 12/2012 | Gillis et al. |
| 2001/0050085 A1 | | 12/2001 | Knudson et al. |
| 2004/0028676 A1 | | 2/2004 | Klein et al. |
| 2004/0073272 A1 | | 4/2004 | Knudson et al. |
| 2004/0153127 A1 | | 8/2004 | Gordon et al. |
| 2005/0098184 A1 | | 5/2005 | Conrad et al. |
| 2005/0126563 A1 | | 6/2005 | van der Burg et al. |
| 2005/0267547 A1 | | 12/2005 | Knudson et al. |
| 2005/0279365 A1 | | 12/2005 | Armijo et al. |
| 2006/0070626 A1 | | 4/2006 | Frazier et al. |
| 2006/0150986 A1 | | 7/2006 | Roue et al. |
| 2006/0201519 A1 | | 9/2006 | Frazier et al. |
| 2006/0207606 A1 | | 9/2006 | Roue et al. |
| 2006/0207607 A1 | | 9/2006 | Hirotsuka et al. |
| 2006/0207608 A1 | | 9/2006 | Hirotsuka et al. |
| 2006/0207612 A1 | | 9/2006 | Jackson et al. |
| 2006/0235264 A1 | | 10/2006 | Vassallo |
| 2007/0144539 A1 | | 6/2007 | van der Burg et al. |
| 2007/0209664 A1 | | 9/2007 | Paraschac et al. |
| 2007/0209665 A1 | | 9/2007 | Gillis et al. |
| 2007/0256693 A1 | | 11/2007 | Paraschac et al. |
| 2008/0023012 A1 | | 1/2008 | Dineen et al. |
| 2008/0027480 A1 | | 1/2008 | van der Burg et al. |
| 2008/0027560 A1 | | 1/2008 | Jackson et al. |
| 2008/0035160 A1 | | 2/2008 | Woodson et al. |
| 2008/0041398 A1 | | 2/2008 | Hegde et al. |
| 2008/0053461 A1 | | 3/2008 | Hirotsuka et al. |
| 2008/0058584 A1 | | 3/2008 | Hirotsuka et al. |
| 2008/0066765 A1 | | 3/2008 | Paraschac et al. |
| 2008/0066769 A1 | | 3/2008 | Dineen et al. |
| 2008/0097380 A1 | | 4/2008 | Li |
| 2008/0208265 A1 | | 8/2008 | Frazier et al. |
| 2009/0044814 A1 | | 2/2009 | Iancea et al. |
| 2009/0131923 A1 | | 5/2009 | Connors et al. |
| 2010/0028026 A1 | | 2/2010 | Inami et al. |
| 2010/0106246 A1 | | 4/2010 | Rousseau et al. |
| 2010/0108077 A1 | | 5/2010 | Lindh et al. |
| 2010/0132719 A1 | | 6/2010 | Jacobs et al. |
| 2010/0234946 A1 | | 9/2010 | Rousseau |
| 2010/0286793 A1 | | 11/2010 | Newman et al. |
| 2011/0094520 A1 | | 4/2011 | Mikhailenok et al. |
| 2011/0100376 A1 | | 5/2011 | Rousseau |
| 2011/0100378 A1 | | 5/2011 | Rousseau |
| 2011/0130249 A1 | | 6/2011 | Mikhailenok et al. |
| 2011/0166673 A1 | | 7/2011 | Patel et al. |
| 2011/0226264 A1 | | 9/2011 | Friedman et al. |
| 2011/0245850 A1 | | 10/2011 | van der Burg et al. |
| 2011/0308530 A1 | | 12/2011 | Gillis et al. |
| 2013/0056009 A1 | | 3/2013 | Mohan et al. |
| 2013/0085546 A1 | | 4/2013 | Bolea et al. |
| 2013/0180528 A1 | | 7/2013 | Zhou et al. |
| 2013/0213409 A1 | | 8/2013 | Podmore et al. |
| 2014/0272781 A1 | * | 9/2014 | Mohan ............ A61B 17/06109 433/76 |
| 2016/0242935 A1 | * | 8/2016 | Amis ................ A61B 17/1714 |

FOREIGN PATENT DOCUMENTS

| | | |
|---|---|---|
| WO | 2009140197 | 11/2009 |
| WO | WO2010045546 | 4/2010 |
| WO | WO2010051195 | 5/2010 |
| WO | WO2011068952 | 6/2011 |
| WO | WO2011123714 | 10/2011 |
| WO | WO2013010169 | 1/2013 |

OTHER PUBLICATIONS

International Searching Authority, International Search Report and Written Opinion for International application No. PCT/US2014/049341, dated Nov. 19, 2014, pp. 1-11.

(56) References Cited

OTHER PUBLICATIONS

International Searching Authority, International Search Report and the Written Opinion, for International Application No. PCT/US2012/046923, dated Nov. 2, 2012, p. 1-18.
File history of U.S. Appl. No. 08/883,220, now U.S. Pat. No. 5,988,171, as of Jun. 3, 2014, filed Jun. 26, 1997. First Named Inventor, Ze'ev Sohn. Title, Methods and Devices for the Treatment of Airway Obstruction, Sleep Apnea and Snoring.
File history of U.S. Appl. No. 10/877,003, now U.S. Pat. No. 7,213,599, as of Jun. 3, 2014, filed Jun. 24, 2004. First Named Inventor, Timothy R. Conrad. Title, Airway Implant.
File history of U.S. Appl. No. 11/757,501, now U.S. Pat. No. 7,703,460, as of Jun. 3, 2014, filed Jun. 4, 2007. First Named Inventor, Timothy R. Conrad. Title, Tongue Implant.
File history of U.S. Appl. No. 12/214,084 as of Jun. 3, 2014, filed Jun. 17, 2008. First Named Inventor, Octavian Iancea. Title, Implantable devices, systems, and methods for maintaining desired orientations in targeted tissue regions.
Woodson et al. Title, Multicenter study of a novel adjustable tongue-advancement device for obstructive sleep apnea. Journal, Title, Otolaryngology and Head and Neck Surgery. Jun. 10, 2010. p. 585-590. 143(4). Sage Publications.
Woodson et al. Title, Response to: Multicenter study of a novel adjustable tongue-advancement device for obstructive sleep apnea. Journal, Title, Otolaryngology and Head and Neck Surgery. 211. p. 1009-1010. 144(6). Sage Publications.
Hamans et al. Title, A novel tongue implant for tongue advancement for obstructive sleep apnea: Feasibility, safety and histology in a canine model. Journal, Title, Journal of Musculoskeletal and Neuronal Interactions. Dec. 29, 2009. p. 100-111. 10(1). Hylonome.

* cited by examiner

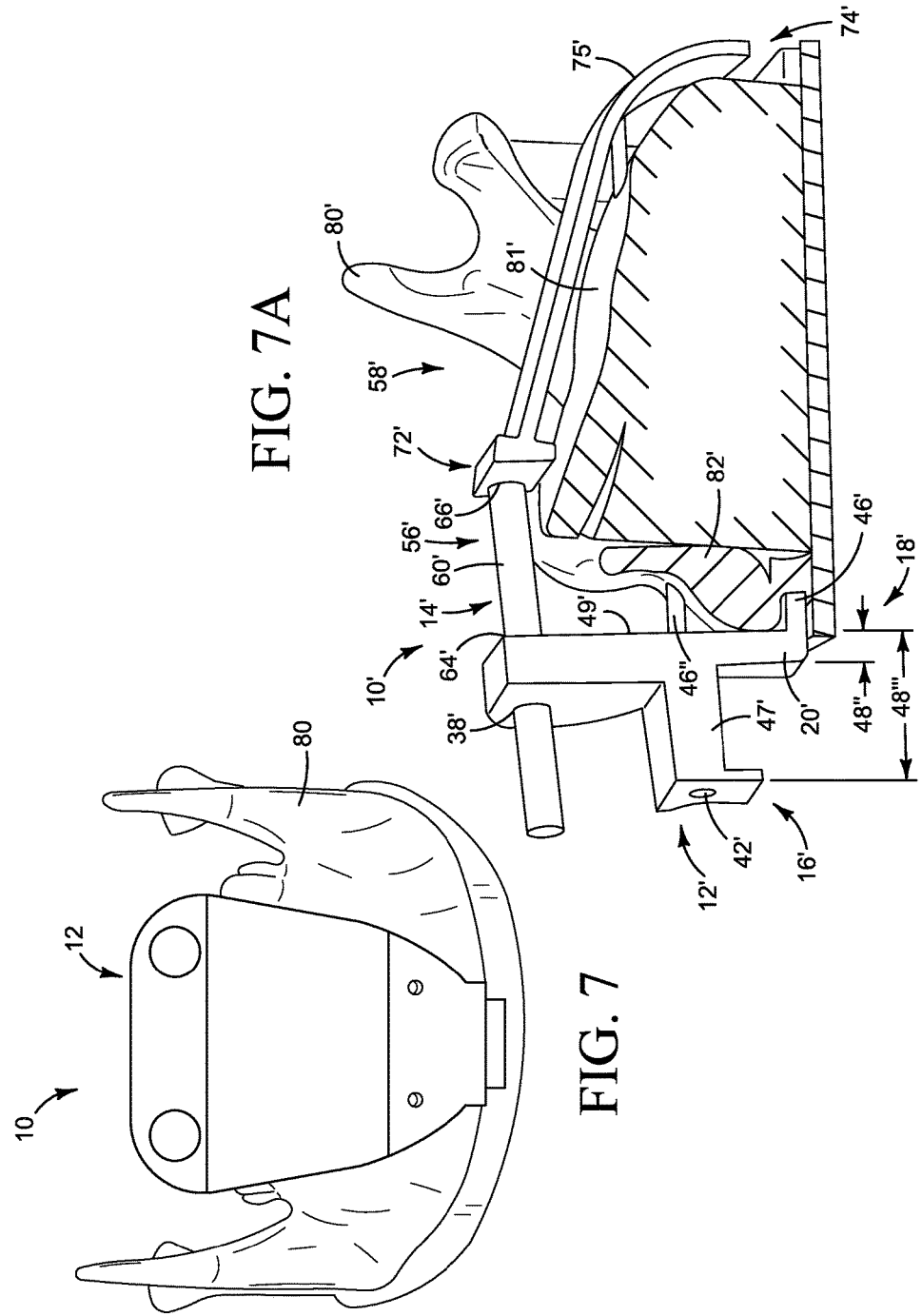

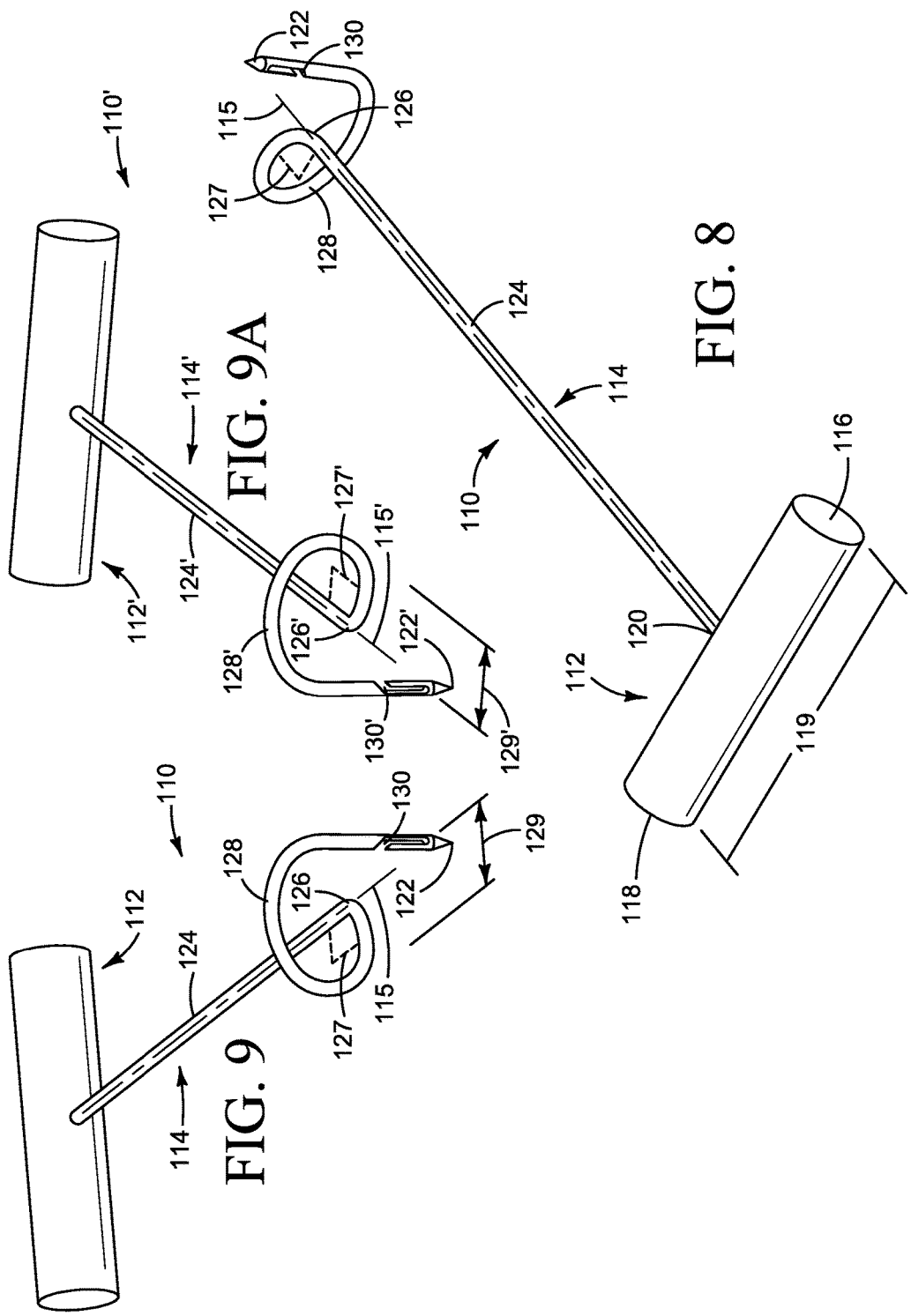

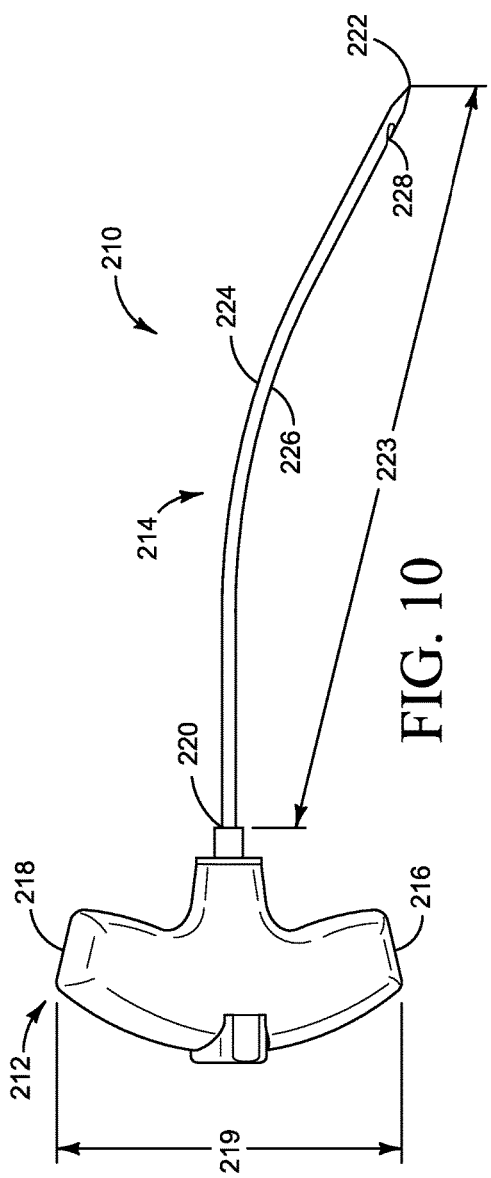
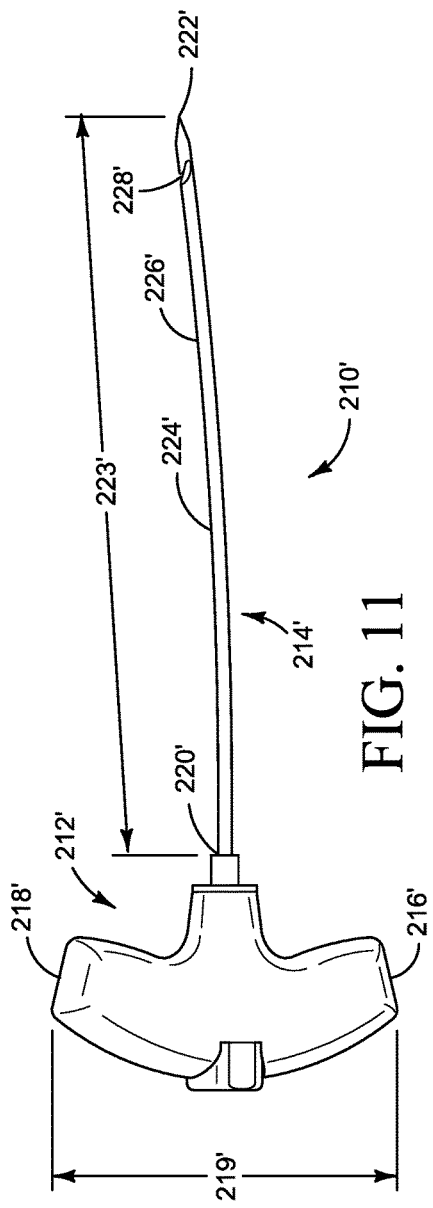
FIG. 10
FIG. 11

DEVICES, KITS, AND METHODS FOR THE TREATMENT OF OBSTRUCTIVE SLEEP APNEA

RELATED APPLICATIONS

This application claims the benefit of U.S. Provisional Application No. 61/793,343, filed Mar. 15, 2013. The disclosure of this related application is hereby incorporated into this disclosure in its entirety.

FIELD

The disclosure relates generally to the field of medical devices, kits containing the medical devices and other devices that facilitate their use, and methods of treatment based on use of the medical devices. More particularly, the disclosure relates to medical devices, kits, and methods useful in the securement of tissue within the body. For example, the medical devices, kits, and methods described herein are useful in the treatment of Obstructive Sleep Apnea (OSA).

BACKGROUND

It is sometimes necessary or desirable to secure a tissue or portion of a tissue within the body of an animal, such as a human. Sling devices are known in the art and can be used to affect such a securement of tissue within the body.

Obstructive Sleep Apnea (OSA) is a clinical disorder in which a partial or complete collapse of soft tissue occurs in the airway during sleep. This leads to a blockage of the airway and impaired breathing during sleep. Mild OSA can lead to fatigue, reduced alertness following sleep, and a general reduction in productivity for the affected individual. Severe OSA can lead to sleep deprivation, hypoxemia, and depression.

OSA can be the result of obesity and/or diabetes. It is believed that about 1 in every 15 Americans are affected by some form of OSA, leading to an estimated $3.4 billion in associated healthcare costs each year.

The art provides various options for the treatment of OSA. Continuous Positive Airway Pressure (CPAP) machines, which supply positive air pressure through a facemask and into the airway during sleep, are used most frequently. The positive air pressure maintains an open airway to prevent apnea and snoring. While these machines are generally considered effective, they are bulky, noisy, and cumbersome to use. Furthermore, use of these machines can be socially awkward for some individuals.

Oral appliances that force the jaw forward to maintain an open airway can also be used. These devices are generally considered to be not as effective as CPAP machines, and can be uncomfortable to use. Furthermore, these devices are frequently ejected from the mouth during sleep, reducing their effectiveness over the entire course of a sleeping period.

Invasive surgical procedures can also be used to treat OSA. Various techniques have been described, including uvulopalatopharyngoplasty (UPPP, maxillomandibular advancement (MMA), and even tracheostomy. Surgical procedures are generally considered to have limited and potentially short-lived effectiveness. Furthermore, many of the procedures require hospitalization and the use of general anesthesia. As a result, these procedures are generally reserved for severe cases of OSA.

The Repose™ System from Medtronic provides a surgical-based tongue suspension procedure that can be performed with or without an adjunct hyoid suspension procedure. These suspension procedures require a surgical incision and dissection of the neck below the mandible. Following implantation of one or more necessary bone screws, sutures are lashed around the tongue and/or hyoid bone and secured with surgical notes. While these procedures offer less complicated solutions than the more invasive surgical procedures above, they still require surgical intervention and suffer from the drawbacks associated with surgical procedures. Furthermore, over time, the sutures used to suspend the tongue and/or hyoid bone may weaken under constant stress and fracture or snap, which may limit the effectiveness of the treatment over time. Lastly, the use of sutures in these procedures necessitates the use of specialized knotting and securement techniques to complete the procedure, which adds an additional opportunity for error and failure in the device and the procedure.

Recent advancements in the art include the use of sling devices for securing the tongue, advancing it forward toward the chin of the patient, and permanently securing the tongue in this new position. These new devices and methods of treatment offer several distinct advantages, including the avoidance of invasive surgical procedures, the use of durable and well-characterized long-term implant materials, and a securement approach that provides long-term stability of the tongue in its new position following treatment.

Considering the advantages of these devices, a need exists for ancillary medical devices, kits, and methods that provide for their reliable and predictable placement.

BRIEF SUMMARY OF DESCRIBED EMBODIMENTS

Various ancillary medical devices useful in the placement of sling devices used in the treatment of OSA are described and illustrated herein. The medical devices include a jig used to create one or more openings through the mandible of a patient at desired positions and angles, a first needle to form a transverse passageway through the tongue, and second and third needles to pull the sling through the one or more passageways created in the mandible. The jig comprises a drill guide and a tongue depressor. The first needle comprises a handle and an elongate shaft that defines a bend and a curve. The second needle comprises a handle and an elongate shaft that defines a curve along its length. The third needle comprises a handle and an elongate shaft that defines a curve along its length.

Various kits are also described and illustrated herein. An example kit comprises one or more of the ancillary medical devices described herein. Another example kit comprises one or more slings and one or more of the ancillary medical devices described herein.

Various methods of treatment are also described herein. An example method of treating Obstructive Sleep Apnea in a patient comprises the following steps: creating an incision in the tissue defining the vestibule of the lower lip of the patient; exposing the bone of the mandible of the patient; placing a jig on the mandible of the patient; confirming placement of the passageways defined on the jig; creating a first opening and a second opening through the mandible of the patient; creating a transverse passageway in the tongue of the patient using a first needle; advancing a second needle through the first opening created in the mandible and through the tongue of said patient; advancing a third needle through the second opening created in the mandible and through the tongue; engaging a sling with the first needle; pulling the first needle and the sling through the transverse passageway; engaging the sling with the second needle; engaging the sling with the third needle; pulling the second needle and the third needle through the openings created in the mandible; pulling the tongue of said patient forward; securing the sling; and closing the incision.

Additional understanding of these medical devices, kits, and methods can be obtained with review of the detailed description, below, and the appended drawings.

BRIEF DESCRIPTION OF THE DRAWINGS

FIG. 7 is a side view of the jig illustrated in FIG. 1 disposed on the display apparatus illustrated in FIG. 6.

FIG. 7A is a partial cross-sectional view of a display apparatus and another jig disposed on the display apparatus.

FIG. 8 is a perspective view of a first needle.

FIG. 9 is another perspective view of the first needle illustrated in FIG. 8.

FIG. 9A is a perspective view of an alternative embodiment of the first needle.

FIG. 10 is a perspective view of a second needle.

FIG. 11 is a perspective view of a third needle.

DETAILED DESCRIPTION OF DESCRIBED EMBODIMENTS

Figure 1:
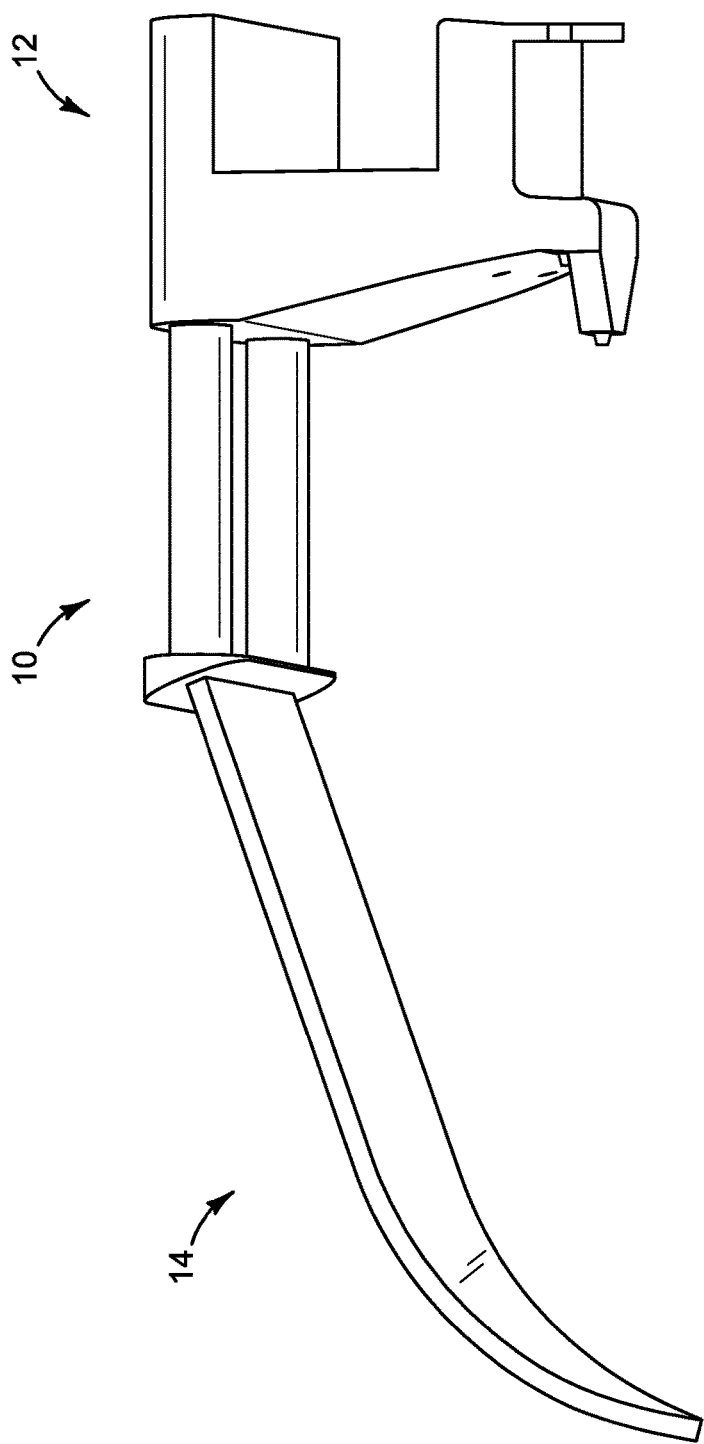
FIG. 1 is a perspective view of a jig.
Figure 2:
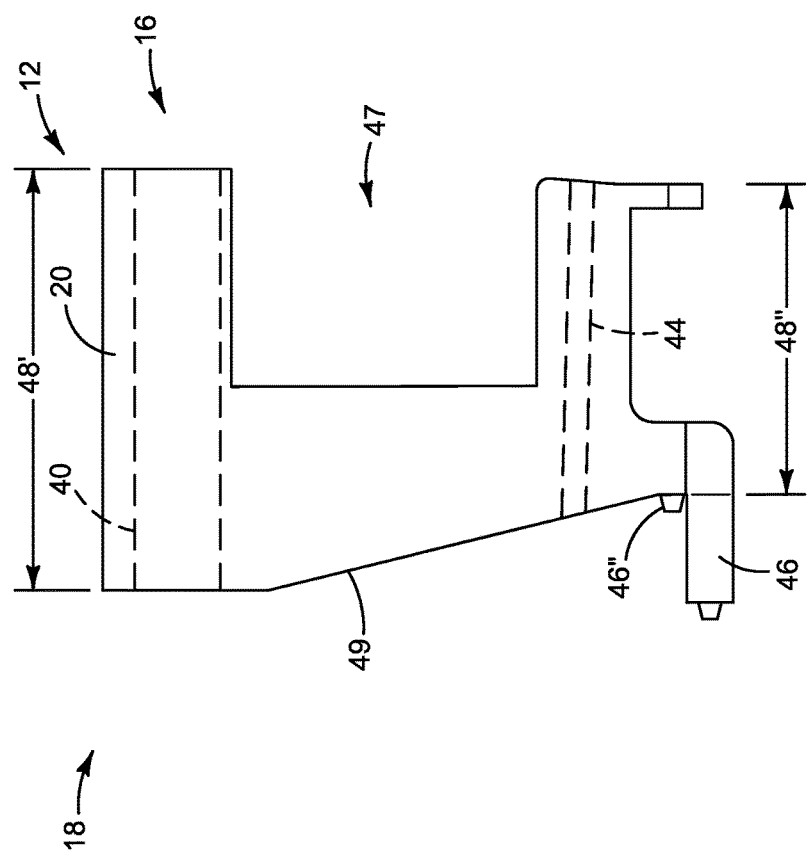
FIG. 2 is a side view of the drill guide of the jig illustrated in FIG. 1, free of the jig.
Figure 4:
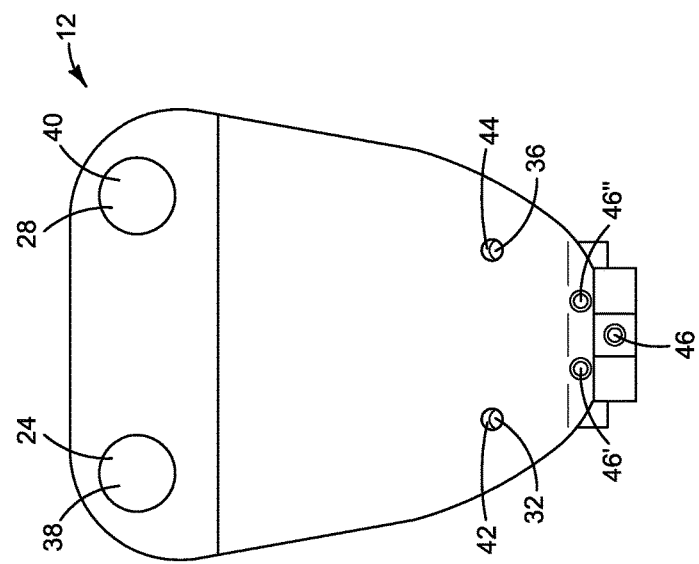
FIG. 4 is a distal end view of the drill guide illustrated in FIG. 2.
Figure 3:
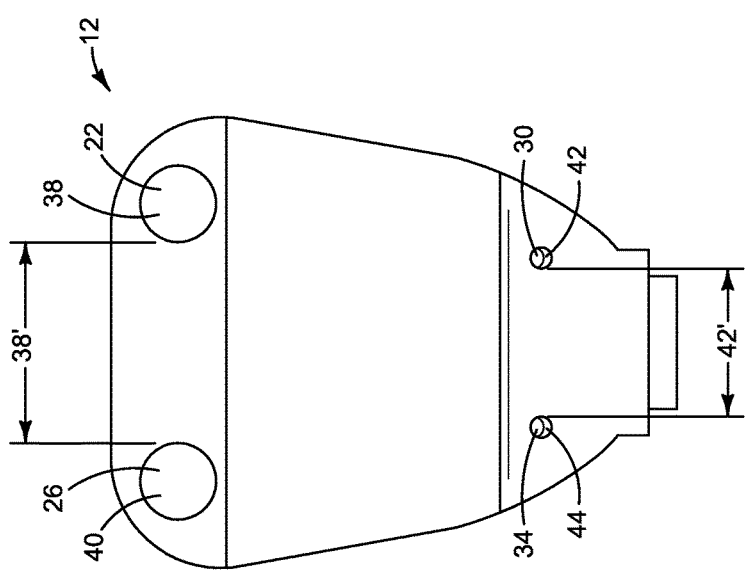
FIG. 3 is a proximal end view of the drill guide illustrated in FIG. 2.
Figure 5:
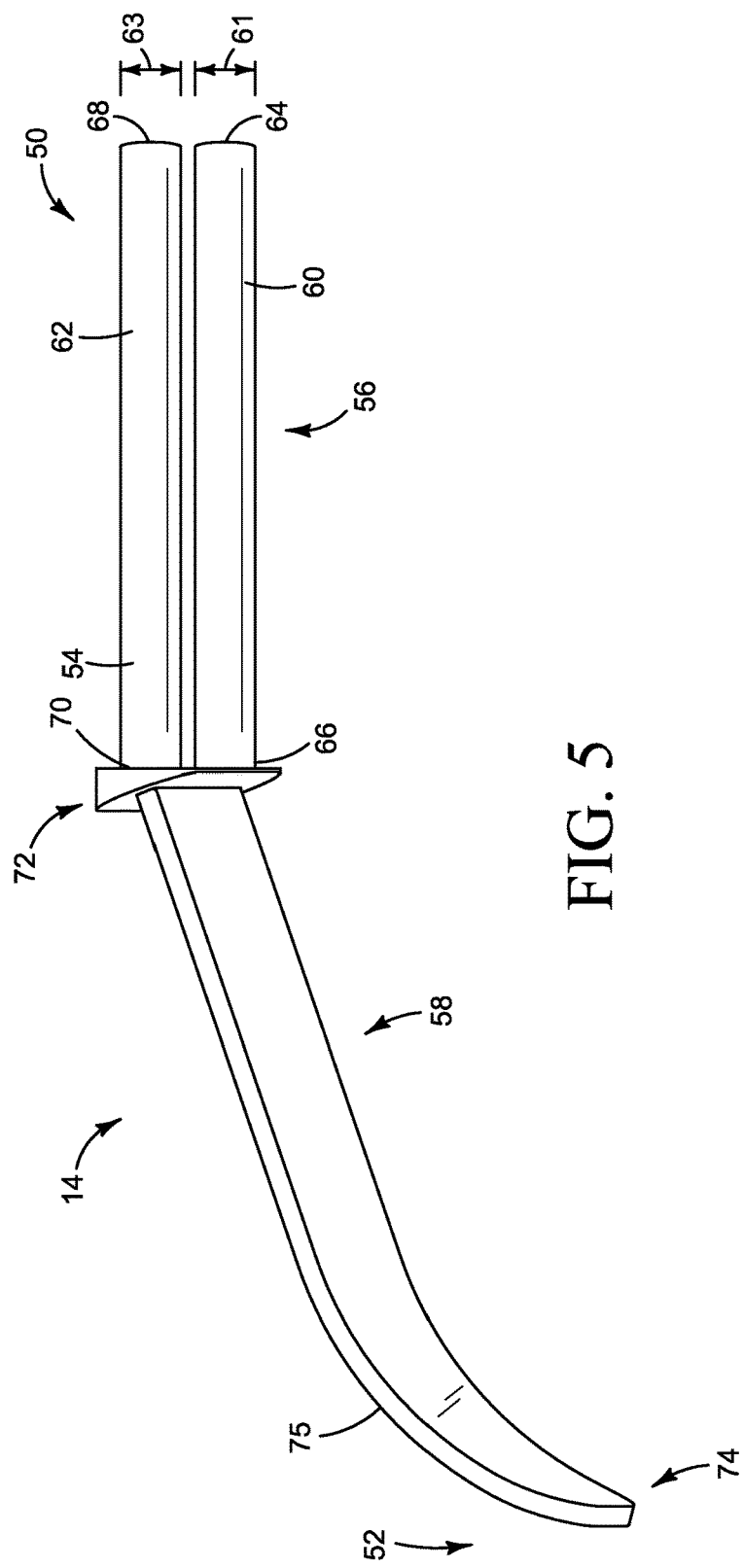
FIG. 5 is a perspective view of the tongue depressor of the jig illustrated in FIG. 1, free of the jig.

The following detailed description and the appended drawings describe and illustrate various medical devices, kits, and methods. The description and drawings are provided to enable one skilled in the art to make and use one or more medical devices, kits, and/or to practice one or more methods. They are not intended to limit the scope of the claims in any manner.

The term "jig" refers to a device, or components, that receives another structure(s), device(s), or instrument(s) and controls the location, motion, and/or the placement of the structure(s), device(s), or instrument(s) during use. Each of the terms "pigtail" and "curve" refers to a length of an element that is arranged in one or more complete or partial spirals, loops, and/or rings. Each of the terms "pigtail" and "curve" does not require regularity in the arrangement of the one or more spirals, loops, and/or rings and does not requires that an entire spiral, loop, and/or ring be formed.

FIGS. 1 through 7 illustrate an embodiment of a jig 10 that comprises a drill guide 12 and a tongue depressor 14.

Drill guide 12 has a proximal end 16, a distal end 18, and a body 20. Body 20 defines a first opening 22, a second opening 24, a third opening 26, a fourth opening 28, a fifth opening 30, a sixth opening 32, a seventh opening 34, an eighth opening 36, a first passageway 38, a second passageway 40, a third passageway 42, a fourth passageway 44, a first protuberance 46, a second protuberance 46', a third protuberance 46", and a notch 47. Each of the first opening 22, third opening 26, fifth opening 30, and seventh opening 34 is disposed on the proximal end 16 of the drill guide 12. Each of the second opening 24, fourth opening 28, sixth opening 32, and eighth opening 36 is disposed on the distal end 18 of the drill guide 12. The first passageway 38 extends from the first opening 22 to the second opening 24. The second passageway 40 extends from the third opening 26 to the fourth opening 28. The third passageway 42 extends from the fifth opening 30 to the sixth opening 32. The fourth passageway 44 extends from the seventh opening 34 to the eighth opening 36.

Each of the first passageway 38 and second passageway 40 is positioned on a first side of the drill guide 12 and each of the third passageway 42 and fourth passageway 44 is positioned on a second side of the drill guide 12 relative to a plane that contains the lengthwise axis of the drill guide 12. In the embodiment illustrated, the inside diameter of each of the first passageway 38 and the second passageway 40 is greater than the inside diameter of each of the third passageway 42 and the fourth passageway 44. However, alternative embodiments can include a first passageway and/or second passageway that has an inside diameter that is greater than, equal to, substantially equal to, or less than the inside diameter of the third passageway and/or fourth passageway. The first passageway 38 is disposed a first distance 38' from the second passageway 40 and the third passageway 42 is disposed a second distance 42' from the fourth passageway 44. The first distance 38' is greater than the second distance 40'. Each of the first distance 38' and the second distance 42' is measured on a plane that is disposed orthogonal to the lengthwise axis of the drill guide 12.

Each of the first passageway 38 and second passageway 40 is adapted to receive a portion of tongue depressor 14, as described below. In the embodiment illustrated, the first passageway 38 is sized and configured to receive a portion of the first shaft 60 of the tongue depressor 14 and the second passageway 40 is sized and configured to receive a portion of the second shaft 62 of the tongue depressor 14. Each of the third passageway 42 and fourth passageway 44 is adapted to receive a portion of a drill bit, as described below. Thus, each of the third passageway 42 and fourth passageway 44 is sized and configured to receive a portion of a drill bit.

In the illustrated embodiment, the first passageway 38 and the second passageway 40 are parallel to each other and the third passageway 42 and the fourth passageway 44 are parallel to each other. The third passageway 42 and the fourth passageway 44 and each have a slight upward angle (e.g., toward the first passageway and second passageway) from the proximal end 16 to the distal end 18 of the drill guide 12. Thus, each of the third passageway 42 and the fourth passageway 44 extend toward a plane that contains the lengthwise axis of the drill guide 12 from the proximal end 16 to the distal end 18 of the drill guide 12.

While the first passageway 38 has been illustrated as disposed a first distance 38' from the second passageway 40 that is greater than a second distance 42' separating the third passageway 42 and the fourth passageway 44, any suitable configuration of the passageways defined by the body of a drill guide is considered suitable. Skilled artisans will be able to select a suitable configuration for the passageways defined by the body of a drill guide according to a particular embodiment based on various considerations, including the structural arrangement at a desired point of treatment. For example, a first passageway can be disposed from a second passageway a first distance and the third passageway can be disposed from the fourth passageway a second distance. The first distance can be greater than, equal to, substantially equal to, or less than the second distance.

While the first passageway 38 and the second passageway 40 have been illustrated as parallel to each other and the third passageway 42 and the fourth passageway 44 have been illustrated as parallel to each other, other configurations are considered suitable. Skilled artisans will be able to select a suitable structural configuration for the passageways defined by a drill guide according to a particular embodiment based on various considerations, including the structural configuration of the tongue depressor of a jig. For example, alternative embodiments could include a first passageway that is not parallel to a second passageway and/or a third passageway that is not parallel to a fourth passageway. Example alternative configurations considered suitable for the third passageway and fourth passageway include a third passageway and fourth passageway that are parallel to the lengthwise axis of the drill guide, a third passageway and/or fourth passageway that extend toward a plane that contains the lengthwise axis of the drill guide from the proximal end to the distal end of the drill guide, a third passageway and/or fourth passageway that extend away from a plane that contains the lengthwise axis of the drill guide from the proximal end to the distal end of the drill guide, a third passageway and/or fourth passageway that extend toward the lengthwise axis of the drill guide from the proximal end to the distal end of the drill guide (e.g., each passageway is angled toward the center of the drill guide), a third passageway and/or fourth passageway that extend away from the lengthwise axis of the drill guide from the proximal end to the distal end of the drill guide (e.g., each passageway is angled away from the center of the drill guide), and any other configuration considered suitable for a particular embodiment.

While the body 20 of the drill guide 12 has been illustrated as defining a first passageway 38 and second passageway 40 that are sized and configured to receive a portion of the tongue depressor 14 and a third passageway 42 and a fourth passageway 44 that are sized and configured to receive a portion of a drill bit, any suitable number of passageways can be defined by the body of a drill guide and can have any suitable size and configuration. Skilled artisans will be able to select a suitable number of passageways to define on a drill guide according to a particular embodiment based on various considerations, including the structural configuration of a tongue depressor of a jig and/or the structural arrangement at a point of treatment. Example number of passageways considered suitable for the body of a drill guide to define that are sized and configured to receive a portion of a tongue depressor and/or a drill bit include one, at least one, two, a plurality, three, four, and any other number considered suitable for a particular embodiment. Example diameters considered suitable include a first passageway and/or second passageway that has a diameter that is equal to, substantially equal to, greater than, or less than the diameter of a third passageway and/or fourth passageway.

Each of the first protuberance 46, second protuberance 46', and third protuberance 46" extends outward and away from the distal end 18 of the drill guide 12. Each of the second protuberance 46' and third protuberance 46" is disposed between the third passageway 42 and the first protuberance 46. The inclusion of one or more protuberances is considered advantageous at least because it provides a mechanism for maintaining the position of the drill guide and/or lower lip during use. However, alternative embodiments can omit a first protuberance, second protuberance, and/or third protuberance from a drill guide.

While the body 20 of the drill guide 12 has been illustrated as defining a first protuberance, a second protuberance, and a third protuberance, the body of a drill guide can define any suitable number of protuberances. Skilled artisans will be able to select a suitable number of protuberances to define on a drill guide according to a particular embodiment based on various considerations, including the structural arrangement at a point of treatment. Example number of protuberances considered suitable for the body of a drill guide to define include one, at least one, two, a plurality, three, four, and any other number considered suitable for a particular embodiment. Optionally, the body of a drill guide can be formed of a first material and each protuberance included on the drill guide can be formed of a second material that is different from, or the same as, the first material. In these embodiments, each protuberance can be an integral component of the drill guide, or a separate component attached to the body of the drill guide using any suitable method of attachment, such as using an adhesive, or using any suitable structure, such as a friction fit between the protuberance and a recess defined by the body of the drill guide.

The body 20 of the drill guide 12 defines the notch 47 on the proximal end 16 of the drill guide 12. The notch 47 extends into the body 20 of the drill guide 12 between the first passageway 38 and the third passageway 42 and from a first side of the body 20 to a second side of the body 20. While the notch 47 has been illustrated as extending from the first side of the drill guide 12 to the second side of the drill guide 12, alternative embodiments can omit the inclusion of a notch, or define a notch that extends between the first side and the second side.

The body 20 has a first length 48' and a second length 48" that defines a sloped surface 49 on the distal end 18 of the drill guide 12 relative to a plane that is orthogonal to the lengthwise axis of the drill guide 12 (e.g., sloped surface 49 extends through, and at an angle to, the lengthwise axis of the drill guide). The first length 48' is measured from the proximal end 16 of the drill guide 12 and along the portion of the body 20 that defines the first passageway 38 and the second passageway 40. The second length 48" is measured from the proximal end 16 of the drill guide 12 and along the portion of the body 20 that defines the third passageway 42 and the fourth passageway 44. In the embodiment illustrated, the first length 48' is greater than the second length 48". Alternatively, a drill guide can define a first length that is equal to, substantially equal to, or less than a second length. For example, the first passageway and/or second passageway defined by the body of a drill guide can have a length that is greater than, equal to, substantially equal to, or less than the length of the third passageway and/or fourth passageway defined by the body of the drill guide.

While the body 20 of the drill guide 12 has been illustrated as having a particular structural arraignment (e.g., that defines a notch 47 and a sloped surface 49), the body of a drill guide can have any suitable structural arrangement. Skilled artisans will be able to select a suitable structural arrangement for a drill guide according to a particular embodiment based on various considerations, including the structural arrangement of a tongue depressor and/or the structural arrangement at a desired point of treatment. In alternative embodiments, the body of a drill guide can omit the inclusion of a notch and/or sloped surface on the distal end of the drill guide. An example alternative embodiment of a drill guide is illustrated in FIG. 7A, and described in more detail below.

Tongue depressor 14 has a proximal end 50, a distal end 52, and a body 54 that defines a track 56 and an elongate member 58. The track 56 extends from the proximal end 50 toward the distal end 52 and has a first shaft 60 and a second shaft 62. First shaft 60 has a first end 64 and a second end 66 and second shaft 62 has a first end 68 and a second end 70. Each of the second end 66 of the first shaft 60 and the second end 70 of the second shaft 62 is attached to elongate member 58.

First shaft 60 is adapted to be received by the first passageway 38 defined by the drill guide 12 and second shaft 62 is adapted to be received by the second passageway 40 defined by the drill guide 12. Thus, the first shaft 60 is parallel to the second shaft 62. However, alternative embodiments can include a first shaft and second shaft that are not parallel and that correspond to the arrangement of the first passageway and second passageway defined by the drill guide. The first shaft 60 is sized and configured to be received by the first passageway 38 and the second shaft 62 is sized and configured to be received by the second passageway 40. In the embodiment illustrated, the first shaft 60 has a length that is greater than the length of the first passageway 38 and the second shaft 62 has a length that is greater than the length of the second passageway 40. The first shaft 60 has an outside diameter 61 that is less than the inside diameter of the first passageway 38 and second shaft 62 has an outside diameter 63 that is less than the inside diameter of the second passageway 40. However, alternative embodiments can include a first shaft that has an outside diameter that is greater than, equal to, or substantially equal to the inside diameter of the first passageway and/or second shaft that has an outside diameter that is greater than, equal to, or substantially equal to the inside diameter of the second passageway. In these embodiments, a friction fit can be accomplished between the drill guide and the tongue depressor as the tongue depressor is advanced into the drill guide such that the tongue depressor is releasably attached to the drill guide.

The elongate member 58 extends from the track 56 to the distal end 52 of the tongue depressor 14. The elongate member 58 has a proximal end 72 and a distal end 74 and the body 54 of the tongue depressor 14 defines a curve 75 between the proximal end 72 and the distal end 74 of the elongate member 58. In the illustrated embodiment, the portion of the elongate member 58 that extends from the proximal end 72 of the elongate member 58 to the curve 75 is disposed at an angle to, and extends away from, a plane that contains the lengthwise axis of the first shaft 60 and the lengthwise axis of the second shaft 62. Curve 75 extends from the angled portion of the elongate member 58 disposed proximal to the curve 75 and away from the plane that contains the lengthwise axis of the first shaft 60 and the lengthwise axis of the second shaft 62. This structural arrangement corresponds to the general anatomy of the portion of a body that is intended to be treated (e.g., tongue of a patient). However, other structural arrangements are considered suitable. For example, alternative embodiments can include an elongate member that omits the inclusion of a curve defined between the proximal end and the distal end of the elongate member and/or that defines a bend between the proximal end and the distal end of the elongate member.

The portion of the elongate member 58 positioned proximal to the curve 75 can be disposed at any suitable angle relative to a plane that contains the lengthwise axis of the first shaft 60 and the lengthwise axis of the second shaft 62 and the curve 75 can have any suitable radius of curvature. Skilled artisans will be able to select a suitable angle and radius of curvature to define on the elongate member of a tongue depressor according to a particular embodiment based on various considerations, including the structural arrangement of the anatomy on which the device is intended to be used. Example angles considered suitable include angles between 0 degrees and 45 degrees, between about 0 degrees and about 45 degrees, angles less than 45 degrees, angles less than about 45 degrees, and any other angle considered suitable for a particular embodiment.

Figure 6:
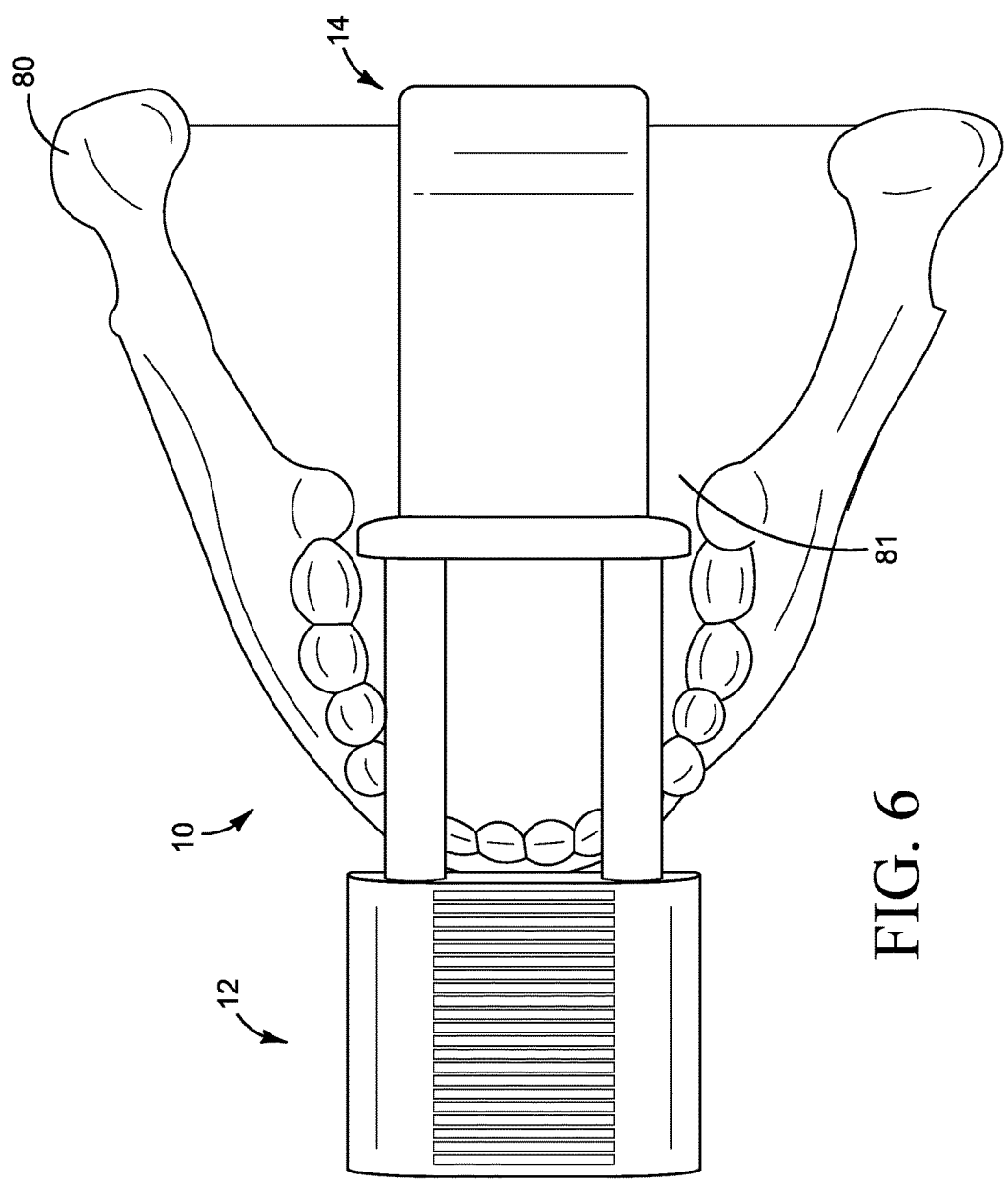
FIG. 6 is a top view of the jig illustrated in FIG. 1 disposed on a demonstration apparatus.

FIGS. 6 and 7 illustrate the jig 10 disposed on a display apparatus that is formed as a human mandible 80 and tongue 81. While the example of a human mandible 80 and tongue 81 has been illustrated, the medical devices, kits, and methods described herein can be used to treat any suitable portion of the body. In use, the first shaft 60 is passed through the first passageway 38 of the drill guide 12 and the second shaft 62 is passed through the second passageway 40 of the drill guide 12. The elongate member 58 is disposed on the tongue 81 and the drill guide 12 is disposed on the mandible 80 of the patient such that the lower lip is retracted and positioned between a surface of the drill guide 12 (e.g., sloped surface 49) and the mandible 80. The drill guide 12 and the tongue depressor 14 are advanced toward one another until each of the third passageway 42 and fourth passageway 44 are disposed below the central incisor tooth root and above the top of the lower lip.

Optionally, one or more apertures can be defined through the body 20 of drill guide 12 that are in communication with the first passageway 38 and/or one or more apertures can be defined through body 20 of drill guide 12 that are in communication with the second passageway 40. Each aperture can include threads that are complementary to threads of a set screw that can be disposed through the aperture to releasably attach, or attach, the tongue depressor 14 to the drill guide 12. For example when first shaft 60 is disposed through first passageway 38 and second shaft 62 is disposed through the second passageway 40, a set screw can be advanced through an aperture in communication with a passageway until the set screw contacts the shaft of the tongue depressor to releasably attach, or attach, the tongue depressor 14 to the drill guide 12. This is considered advantageous at least because it provides a mechanism for maintaining a desired position of the jig 10 during use.

While one or more apertures and one or more set screws have been described, a tongue depressor can be releasably attached, or attached, to a drill guide using any suitable method or structure, and skilled artisans will be able to select suitable method and/or structure to attach, or releasably attach, a tongue depressor to a drill guide according to a particular embodiment based on various considerations, including the structural arrangement of a track. Example methods and structures considered suitable include, but are not limited to, using snap fit configurations, using adhesives, and any other method or structure considered suitable for a particular application.

While the body 54 of the tongue depressor 14 has been illustrated as defining a track 56 having a first shaft 60 and a second shaft 62, the body of a tongue depressor can define a track with any suitable number of shafts. Skilled artisans will be able to select a suitable number of shafts to define on the track of a tongue depressor according to a particular embodiment based on various considerations, including the structural configuration of a drill guide of a jig and/or the structural arrangement at a point of treatment. Example number of shafts considered suitable for the body of a tongue depressor to define include one, at least one, two, a plurality, three, four, and any other number considered suitable for a particular embodiment. An example alternative embodiment of a tongue depressor is illustrated in FIG. 7A, and described in more detail below.

While the body 54 of the tongue depressor 14 has been illustrated as having a particular structural arrangement (e.g., that defines a track 56 and an elongate member 58), the body of a tongue depressor can have any suitable structural arrangement. Skilled artisans will be able to select a suitable structural arrangement for a tongue depressor according to a particular embodiment based on various considerations, including the arrangement of a drill guide and/or the structural arrangement at a desired point of treatment. For example, each shaft defined by a tongue depressor can have a length that is less than, equal to, or substantially equal to, the length of a passageway defined by a drill guide.

Each of the drill guide 12 and tongue depressor 14 can be formed of any suitable material, and skilled artisans will be able to select a suitable material to form a drill guide and tongue depressor of a jig according to a particular embodiment based on various considerations, including the type of treatment intended to be performed. Example materials considered suitable to form a drill guide and/or a tongue depressor of a jig include biocompatible materials, materials that can be made biocompatible, metals such as stainless steel, titanium, nickel-titanium alloys (e.g., Nitinol), polymers, Pebax (Pebax is a registered trademark of Ato Chimie Corporation of Allee des Vosges, Courbevoie, France), nylon, polyethylene, polyurethane, polytetrafluoroethylene (PTFE), ePTFE, silicone, and any other material considered suitable for a particular application. For example, a drill guide can be formed of a first material and the tongue depressor can be formed of a second material. The first material can be the same as, or different than, the second material.

FIG. 7A illustrates another jig 10' disposed on a display apparatus that is formed as a human mandible 80'. The display apparatus illustrates the human mandible 80', the tongue 81', and the lower lip 82'. Jig 10' is similar to jig 10 illustrated in FIGS. 1 through 7 and described above, except as detailed below. Reference numbers in FIG. 7A refer to the same structural element or feature referenced by the same number in FIGS. 1 through 7, offset by '. Thus, jig 10' comprises a drill guide 12' and a tongue depressor 14'.

In the embodiment illustrated, the drill guide 12' omits the inclusion of a second passageway (e.g., second passageway 40), fourth passageway (e.g., fourth passageway 44), and a third protuberance (e.g., third protuberance 46"). In addition, alternative to defining a first notch (e.g., notch 47) and a sloped surface (e.g., sloped surface 49), the body 20' of the drill guide 12' defines a protuberance 47' and a flat distal surface 49' (e.g., orthogonal to the lengthwise axis of the drill guide 12').

The protuberance 47' extends from the proximal end 16' of the drill guide 12' and away from the distal end 18' of the drill guide 12'. The drill guide 12' has a first length 48" and a second length 48"'. The first length 48" extends from the proximal end 16' to the distal end 18' of the drill guide 12'. The second length 48"' extends from the proximal end of the protuberance 47' to the distal end 18' of the drill guide 12'. In the embodiment illustrated, the first length 48" is less than the second length 48"'. Thus, the first passageway 38' has a length that is less than the length of the third passageway 42'.

In the illustrated embodiment, the tongue depressor 14' omits the inclusion of a second shaft (e.g., second shaft 62) and includes a first shaft 60' that extends from a first end 64' to a second end 66'. The first shaft 60' is disposed on the center of the proximal end 72' of the elongate member 58'. However, alternative embodiments can include a first shaft 60' that is offset from the center of the proximal end 72' of the elongate member 58'. The elongate member 58' of tongue depressor 14' defines a curve 75' between the proximal end 72' and the distal end 74' of the elongate member 58'. The curve 75' has a radius of curvature that is less than the radius of curvature of the curve 75 defined on the elongate member 14 illustrated in FIGS. 1, 5, 6, and 7.

In use, as illustrated in FIG. 7A, the first shaft 60' is passed through the first passageway 38' of the drill guide 12'. The elongate member 58' is disposed on the tongue 81' and the drill guide 12' is disposed on the mandible 80' such that the lower lip 82' is retracted and positioned between a surface of the drill guide 12' (flat distal surface 49') and the mandible 80'. The drill guide 12' and the tongue depressor 14' are advanced toward one another until the third passageway 42' is disposed below the central incisor tooth root and above the top of the lower lip 82'.

FIGS. 8 and 9 illustrate a first needle 110 that comprises a handle 112 and an elongate shaft 114.

Handle 112 has a first end 116 and a second end 118 and an axial length 119 that extends from the first end 116 to the second end 118. In the illustrated embodiment, the handle 112 has a cylindrical cross-sectional configuration that extends from the first end 116 to the second end 118. However, other cross-sectional configurations are considered suitable, such as rectangular, square, oval, cross-sectional configurations that vary along the axial length of the handle, and any other cross-sectional configuration considered suitable for a particular embodiment.

Elongate shaft 114 has a lengthwise axis 115, a first end 120, a tapered second end 122, and a body 124 that defines a bend 126, a curve 128, and a notch 130. The first end 120 is attached to handle 112 such that elongate shaft 114 extends at an angle to the axial length 119 of handle 112. The elongate shaft 114 can be disposed at any suitable angle to the handle (e.g., substantially 90 degree angle, 90 degree angle). The first end 120 can be attached to the handle 112 using any suitable method or structure, such as using adhesive, threaded connections, press fit configurations, and any other method or structure considered suitable for a particular embodiment.

Bend 126 is defined between the first end 120 and the tapered second end 122 of the elongate shaft 114. The bend 126 is defined at an angle 127 relative to the lengthwise axis 115 of the elongate shaft 112. In the illustrated embodiment, the bend 126 is defined at a substantially 90 degree angle 127 relative to the lengthwise axis 115. The bend 126 can be formed on elongate shaft 114 using any suitable method and/or structure. For example, the bend 126 can be formed on elongate shaft 114 by placing the elongate shaft 114 on a mandrel and applying a force on the portion of the elongate shaft disposed proximal to the mandrel while maintaining the position of the portion of the elongate shaft disposed distal to the mandrel.

While bend 126 has been illustrated as defined at substantially a 90 degree angle, a bend can be defined at any suitable angle to the lengthwise axis of an elongate shaft, and skilled artisans will be able to select a suitable angle to define a bend relative to the lengthwise axis of an elongate shaft according to a particular embodiment based on various considerations, including the structural arrangement at a treatment site. Example angles considered suitable to define a bend relative to the lengthwise axis of an elongate shaft include, but are not limited to, angles between about 1 degree and about 180 degrees, between about 20 degrees and about 160 degrees, between about 45 degrees and about 135 degrees, about 90 degrees, at a substantially 90 degree angle, at a 90 degree angle, and any other angle considered suitable for a particular application.

Curve 128 is defined distal to the bend 126, extends about the lengthwise axis 115 (e.g., orbits the lengthwise axis), and defines an outside diameter 129 measured along a plane that is orthogonal to the lengthwise axis 115 of the elongate shaft 114. In the illustrated embodiment, the curve 128 extends about lengthwise axis 115 of the elongate shaft 114 about 270 degrees such that the tapered second end 122 of the elongate shaft 114 and a portion of curve 128 is disposed on a plane that extends through, and at an angle to, the lengthwise axis 115 of elongate shaft 114. The curve 128 is configured such that it defines a pigtail configuration. In the embodiment illustrated, the curve 128 extends from a location distal to the bend 126 in a counter-clockwise direction relative to the lengthwise axis 115 of the elongate shaft 114 to a location proximal to the notch 130.

While the a portion of curve 128 has been illustrated as disposed on a plane that extends at an angle to the lengthwise axis 115 of elongate shaft 114, a curve can have any suitable structural arrangement. Skilled artisans will be able to select a suitable structural arrangement for a curve according to a particular embodiment based on various considerations, including the structural arrangement at a treatment site. Example structural arrangements considered suitable for a curve include, but are not limited to, positioning an entire curve on a plane that extends orthogonal to the lengthwise axis of an elongate shaft, positioning a portion of a curve on a plane that extends orthogonal to the lengthwise axis of an elongate shaft, positioning an entire curve and a tapered distal end on a plane that extends orthogonal to the lengthwise axis of an elongate shaft, positioning a portion of a curve and a tapered distal end on a plane that extends orthogonal to the lengthwise axis of an elongate shaft, positioning a portion, or the entirety, of a curve on a plane that extends through, and at an angle (e.g., between about 1 degree and about 180 degrees, between about 45 degrees and about 135 degrees, at a 45 degree angle, at about a 45 degree angle, at a substantially 45 degree angle, at a 90 degree angle, at a substantially 90 degree angle, at about a 90 degree angle) to the lengthwise axis of an elongate shaft, and any other structural arrangement considered suitable for a particular application. Alternative to a curve extending about the lengthwise axis 115 of the elongate shaft 114 about 270 degrees, a curve can extend about the lengthwise axis of an elongate shaft any suitable distance, such as distances that define a curve that extends about the lengthwise axis of an elongate shaft equal to, substantially equal to, or about 45 degrees, 90 degrees, 135 degrees, 180 degrees, 225 degrees, 270 degrees, 315 degrees, 360 degrees, and any other distance considered suitable for a particular embodiment.

Curve 128 can define any suitable outside diameter 129 measured along a plane that is orthogonal to the lengthwise axis 115 of elongate shaft 114. Skilled artisans will be able to select a suitable outside diameter for a curve according to a particular embodiment based on various considerations, including the width of the tongue of a patient. Example diameters considered suitable to define a curve include, but are not limited to, diameters that are between about 1% and 100% of the width of an average human tongue, diameters that are between about 10% and 90% of the width of an average human tongue, diameters that are between about 20% and 80% of the width of an average human tongue, diameters that are between about 30% and 70% of the width of an average human tongue, diameters that are between about 40% and 60% of the width of an average human tongue, diameters that are about 50% of the width of an average human tongue, diameters that are 50% of the width of an average human tongue, diameters that are substantially 50% of the width of an average human tongue, diameters that are between about 0.25 inches and about 4.0 inches, diameters that are between about 0.50 inches and about 3.0 inches, diameters that are between about 0.75 inches and about 2.0 inches, diameters that are between about 1.0 inch and about 1.75 inches, diameters that are about 1.0 inch, diameters that are 1.0 inch, diameters that are substantially 1.0 inch, and any other diameter considered suitable for a particular application. As used herein, the width of an average human tongue is equal to, substantially equal to, or about 2.0 inches.

Notch 130 is disposed between the curve 128 and the tapered second end 122 of the elongate shaft 114 and extends into the body 124 of the elongate shaft 114 toward the lengthwise axis 115 of the elongate shaft 114 (e.g., center of the body 124 of the elongate shaft) and toward the tapered second end 122. The notch 130 extends into the body 124 a first length and toward the tapered second end 122 a second length. In the illustrated embodiment, the second length is greater than the first length. However, alternative embodiments can include a notch that has a first length that is greater than, equal to, or substantially equal to, the second length.

The handle 112 and the elongate shaft 114 of a first needle 110 can be formed of any suitable material, and skilled artisans will be able to select a suitable material for a handle and an elongate shaft of a needle according to a particular embodiment based on various considerations, including the treatment intended to be performed. Example materials considered suitable to form a handle and an elongate shaft of a needle include biocompatible materials, materials that can be made biocompatible, metals such as stainless steel, titanium, nickel-titanium alloys (e.g., Nitinol), polymers, Pebax (Pebax is a registered trademark of Ato Chimie Corporation of Allee des Vosges, Courbevoie, France), nylon, polyethylene, polyurethane, polytetrafluoroethylene (PTFE), ePTFE, silicone, and any other material considered suitable for a particular application. For example, the handle of a needle can be formed of a first material and the elongate shaft of the needle can be formed of a second material. The first material can be the same as, or different than, the second material. For example, the first material can be a polymer and the second material can be a metal.

FIG. 9A illustrates an alternative embodiment of a first needle 110'. First needle 110' is similar to first needle 110 illustrated in FIGS. 8 and 9 and described above, except as detailed below. Reference numbers in FIG. 9A refer to the same structural element or feature referenced by the same number in FIGS. 8 and 9, offset by '. Thus, first needle 110' comprises a handle 112' and an elongate shaft 114'.

In the illustrated embodiment, the curve 128' is defined distal to the bend 126', extends about the lengthwise axis 115' (e.g., orbits the lengthwise axis), and defines an outside diameter 129' measured along a plane that is orthogonal to the lengthwise axis 115' of the elongate shaft 114'. In the illustrated embodiment, the curve 128' extends about lengthwise axis 115' of the elongate shaft 114' about 180 degrees such that the tapered second end 122' of the elongate shaft 114' and a portion of curve 128' is disposed on a plane that extends orthogonal to the lengthwise axis 115' of elongate shaft 114'. The curve 128' is configured such that it defines a pigtail configuration. In addition, in the embodiment illustrated, the curve 128' extends from a location distal to the bend 126' in a clockwise direction relative to the lengthwise axis 115' of the elongate shaft 114' to a location proximal to the notch 130'.

FIG. 10 illustrates a second needle 210. Second needle 210 is similar to first needle 110 illustrated in FIGS. 8 and 9 and described above, except as detailed below. Reference numbers in FIG. 10 refer to the same structural element or feature referenced by the same number in FIGS. 8 and 9, offset by 100. Thus, second needle 210 has a handle 212 and an elongate shaft 214.

In the embodiment illustrated, the handle 212 has a first end 216, a second end 218, and an axial length 219 that extends from the first end 216 to the second end 218. The cross-sectional configuration of handle 212 varies along the axial length 219 of the handle 212 and defines an ergonomical grip with two finger flanges.

Elongate shaft 214 has a first end 220, a tapered second end 222, a length 223 that extends from the first end 220 to the second end 222, and a body 224. First end 220 is attached to handle 212 using any suitable method or structure, such as those described herein. For example, the elongate shaft 214 can define a bend between the first end 220 and the second end 222 that is disposed within a recess defined by the handle 212 and an adhesive can be applied within the recess to achieve attachment of the elongate shaft 214 to the handle 212.

Alternative to defining a bend (e.g., bend 126), a curve (e.g., curve 128), and a notch (e.g., notch 130) as illustrated in FIGS. 8 and 9, the body 224 of the elongate shaft 214 defines a curve 226 and a notch 228. The curve 226 is defined along a portion of the length 223 of elongate shaft 214 that extends from the tapered second end 222 and toward the first end 220. Alternatively, a curve 226 defined by an elongate shaft 214 can be defined along the entire length of the elongate shaft 214 (e.g., from the first end 220 to the tapered second end 222, from the handle 212 to the tapered second end 222).

Notch 228 is disposed between the first end 220 and the tapered second end 222 and extends into body 224 toward the lengthwise axis of the elongate shaft 214 (e.g., center of the body 224 of the elongate shaft 214) and toward the tapered second end 222. The notch 228 extends into the body 224 a first length and toward the tapered second end 222 a second length. In the illustrated embodiment, the second length is greater than the first length.

FIG. 11 illustrates a third needle 210'. Third needle 210' is similar to the second needle 210 illustrated in FIG. 10 and described above, except as detailed below. Reference numbers in FIG. 11 refer to the same structural element or feature referenced by the same number in FIG. 10, offset by '. Thus, third needle 210' has a handle 212' and an elongate shaft 214'.

In the illustrated embodiment, the curve 226' is defined along the entire length of the elongate shaft 214' that extends from the handle 212' (e.g., from the handle 212' to the tapered second end 222').

While the first needle 110, second needle 210, and third needle 210' have been illustrated as having an elongate shaft with a tapered second end and a circular cross-sectional configuration, the elongate shaft of a needle can have any suitable structural configuration. Skilled artisans will be able to select a suitable cross-sectional configuration for the elongate shaft of a needle according to a particular embodiment based on various considerations, including the treatment intended to be performed. Example cross-sectional configurations considered suitable include rectangular, square, oval, cross-sectional configurations that vary along the axial length of the elongate shaft, and any other cross-sectional configuration considered suitable for a particular embodiment. Alternative to an elongate shaft having a tapered second end, an elongate shaft can have a second end that is curved, that is adapted to be atraumatic, and any other configuration considered suitable for a particular embodiment.

Figure 12:
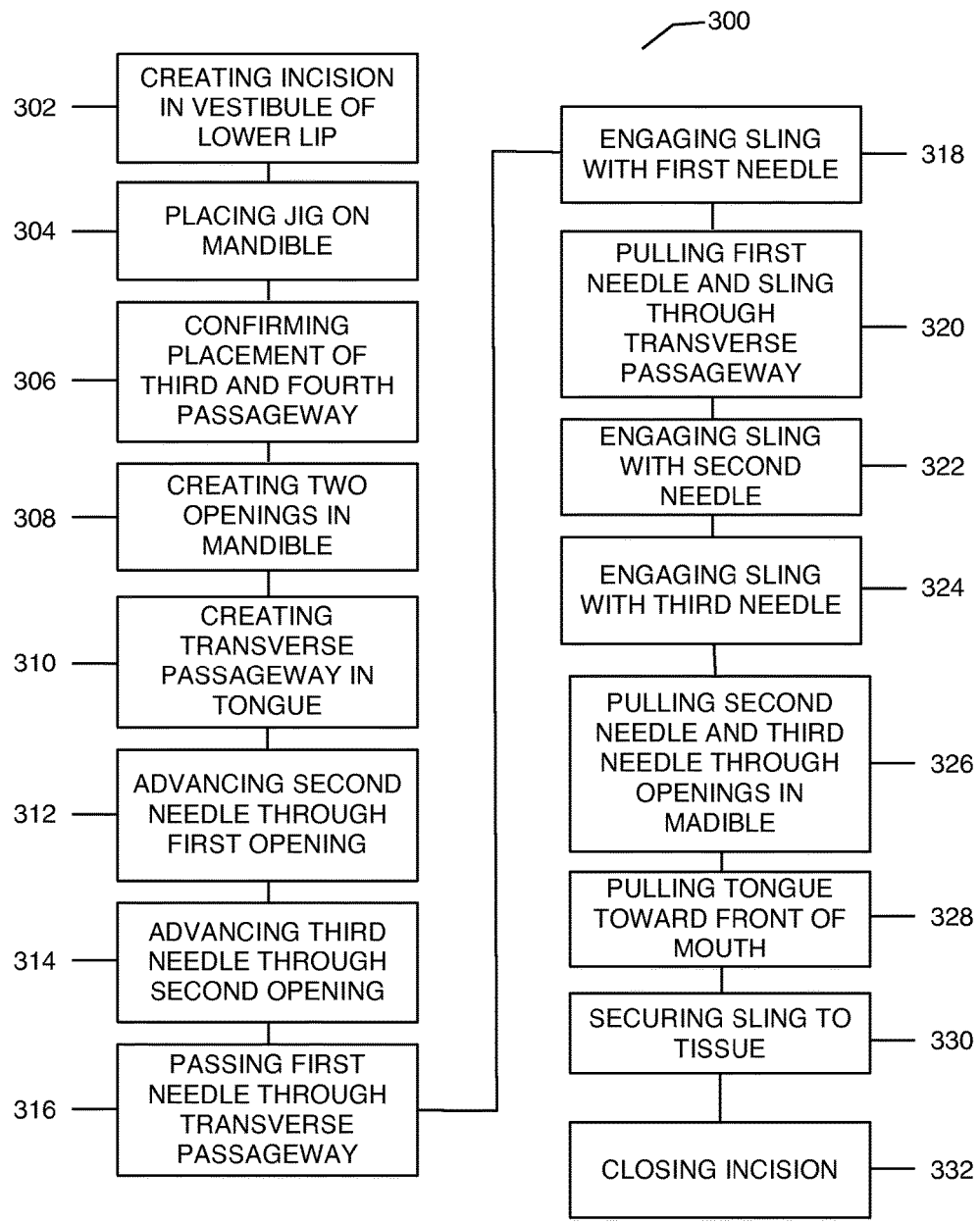
FIG. 12 is a flowchart representation of a method of treating Obstructive Sleep Apnea.

FIG. 12 is a flowchart representation of a method 300 of treating Obstructive Sleep Apnea (OSA) in a patient using a sling. Performance of the method results in securement of the tongue of an animal, such as a human, via the sling being looped through the tongue and secured to the mandible. With the tongue secured in this manner, it is expected that the individual being treated will experience fewer and/or reduced symptoms associated with OSA.

An initial step 302 comprises creating an incision in the tissue that defines the vestibule of the lower lip of the patient to expose the mandible (e.g., mentum of the mandible). The incision can be made at any suitable location that allows for the drilling of holes, as described below. Any suitable technique and tool can be used to perform this step, including a scalpel or other cutting instrument. Alternatively, an incision can be made below the tissue that defines the vestibule of the lower lip of the patient to expose the mandible (e.g., below the chin, above the chin).

An optional step comprises exposing the treatment site (e.g., the tissue forming the vestibule of the lower lip of the patient). This optional step can be accomplished prior to step 302 and using any suitable tool, such as a Jenning's mouth retractor. Another optional step comprises administering a medication to the patient. This optional step can be accomplished prior to step 302 and using any suitable medication (e.g., lidocaine, epinephrine). For example, the lower lip of the patient can be grasped and the sub-labial region of the gingiva groove of the mandible can be infiltrated with 1% lidocaine with 1:100,000 epinephrine. Another optional step comprises exposing the bone of the mandible. This optional step can be accomplished by moving the tissue located adjacent the incision made in step 302. Any suitable tool can be used to expose the mandible and move the tissue (e.g., freer elevator, forceps). Another optional step comprises preserving a cuff of gingiva to facilitate closure of the incision.

Another step 304 comprises placing a jig, such as jig 10, on the mandible of the patient. This step can be accomplished by contacting a protuberance of the drill guide (e.g., first protuberance 46, second protuberance 46', third protuberance 46") to the mandible, or the tissue disposed over the mandible, and the tongue depressor to the tongue. An optional step comprises placing a distally directed force (e.g., toward tongue of patient) on the drill guide and a proximally directed force (e.g., toward drill guide) on the tongue depressor such that the drill guide and tongue depressor are advanced toward one another. Another optional step comprises retracting the lower lip of the patient (e.g., such that it is disposed below a passageway and/or protuberance defined by the drill guide, such that the interior surface of the lower lip is directed toward a surface of the drill guide). Use of a jig, such as jig 10, is considered advantageous at least because it is expected to reduce risk of error in the positioning of the openings intended to be formed through the mandible. Another optional step comprises releasably attaching the tongue depressor to the drill guide. In embodiments that include one or more set screws that are adapted to contact a shaft of a tongue depressor, another optional step comprises advancing each set screw into and through the aperture defined by the drill guide until the set screw contacts the shaft.

While method 300 has been described as being completed with jig 10, any suitable device(s) can be used to complete the methods, steps, optional steps, and/or alternative steps described herein. Skilled artisans will be able to select a suitable device(s) to complete a method, step, optional step, and/or alternative step according to a particular embodiment based on various considerations, including the treatment intended to be performed. Example devices considered suitable to complete the methods, steps, optional steps, and/or alternative steps described herein include jig 10, jig 10', first needle 110, first needle 110', second needle 210, third needle 210', and any other device considered suitable for a particular application.

Another step 306 comprises confirming placement of the third passageway and fourth passageway defined by the drill guide. This step is considered advantageous to avoid creating openings in the mandible in undesirable locations. For example, this step can be accomplished by confirming that each of the third passageway and fourth passageway is disposed below the root of the central incisor tooth (e.g., each of the third passageway and fourth passageway is below the exposed incisor at least, or greater than, two times the height of the exposed incisor). In embodiments in which the jig omits the inclusion of a fourth passageway (e.g., jig 10'), this step 306 can alternatively comprise confirming placement of the third passageway.

Another step 308 comprises creating a first opening and a second opening in the mandible of the patient, such as at the mental protuberance or chin. This step can be accomplished using any suitable technique, including standard drilling techniques and at any suitable location on the mandible, such as in the paramedian position. For example, the following optional steps can be completed. An optional step comprises advancing a drill bit having any suitable diameter (e.g., 3 millimeter drill bit) through the third passageway defined by the drill guide and through the outer and inner cortices of the mandible. Another optional step comprises withdrawing the drill bit from the third passageway. Another optional step comprises advancing the drill bit through the fourth passageway defined by the drill guide and through the outer and inner cortices of the mandible. Another optional step comprises withdrawing the drill bit from the fourth passageway. It is considered advantageous for the third passageway and the fourth passageway to be as close together as possible while retaining distinctness of the openings that are created to facilitate tightening of the sling, as described below. Optionally, step 308 can be completed in two separate steps. A first step comprises creating a first opening in the mandible of a patient and a second step comprises creating a second passageway in the mandible of the patient. In embodiments in which the jig omits the inclusion of a fourth passageway (e.g., jig 10'), step 308 can alternatively comprise creating a first opening in the mandible of the patient and can be accomplished as described above. When a single opening is created in the mandible of the patient the drill bit can have an outside diameter that is greater than 3 millimeters such that both the second needle and the through needle can be advanced through the opening.

An optional step comprises introducing a placement rod in the third passageway and through the first opening formed in the mandible after it has been created such that movement of the jig 10 is eliminated, or reduced, relative to the fourth passageway and each of the fourth passageway and the subsequently created second opening is positioned at a desired location relative to the third passageway and first opening. Another optional step comprises withdrawing the placement rod from the third passageway and the first opening formed in the mandible. Another optional step comprises removing the jig from the mandible. This optional step can be accomplished by applying a proximally directed force on the drill guide and/or a distally directed force on the tongue depressor such that the drill guide is advanced away from the tongue depressor. Subsequently, the jig can be removed from the mandible and the tongue. In embodiments that include one or more set screws that are adapted to contact a shaft of a tongue depressor, another optional step comprises advancing each set screw out of and through the aperture defined by the drill guide until the set screw if free of contact with the shaft.

Another step 310 comprises creating a passageway in the tongue of a patient such that the passageway lies on a plane that is transverse to the longitudinal axis of the tongue. Any suitable technique and tool can be used to perform this step, including a needle (e.g., first needle 110, first needle 110') or other tunneling instrument. In embodiments in which the first needle is used to create the transverse passageway in the tongue, an optional step comprises penetrating the tissue of the tongue (e.g., the dorsal tongue posterior to the circumvallate papillae). Another optional step comprises rotating the first needle to create the passageway in the tongue. Depending on the device used, this optional step can be accomplished by rotating the first needle in a clockwise or counter-clockwise direction.

Another step 312 comprises advancing the second needle 210 through the first of the two openings in the mandible such that the second needle extends through the entire opening and through a portion of the tongue of the patient, with a portion of the device (e.g., first end 220) disposed outside of the opening and adjacent the chin and another portion of the device (e.g., tapered second end 222) disposed outside of the opening and adjacent the tongue. For example, the second needle 210 can be advanced such that it is advanced through one of the openings (e.g., left dorsal puncture site) of the transverse passageway created in step 310. An optional step comprises applying a proximally directed force on the first needle to advance the tongue toward the mandible. This optional step can be completed subsequent to step 310 and/or concurrent with step 312.

In embodiments in which the jig omits the inclusion of a fourth passageway (e.g., jig 10'), step 312 can alternatively comprise advancing the second needle 210 through the opening created in the mandible such that the second needle extends through the entire opening and through a first portion of the tongue of the patient, with a portion of the device (e.g., first end 220) disposed outside of the opening and adjacent the chin and another portion of the device (e.g., tapered second end 222) disposed outside of the opening and adjacent the tongue. For example, the second needle 210 can be advanced such that it is advanced through one of the openings (e.g., left dorsal puncture site) of the transverse passageway created in step 310.

Another step 314 comprises advancing the third needle 210' through the second of the two openings in the mandible such that the third needle 210' extends through the entire second opening and through a portion of the tongue of the patient, with a portion of the device (e.g., first end 220') disposed outside of the second opening and adjacent the chin and another portion of the device (e.g., tapered second end 222') disposed outside of the second opening and adjacent the tongue. For example, the third needle 210' can be advanced such that it is advanced through one of the openings (e.g., right dorsal puncture site) of the transverse passageway created in step 310. An optional step comprises applying a proximally directed force on the first needle to advance the tongue toward the mandible. This optional step can be completed subsequent to step 312 and/or concurrent with step 314.

In embodiments in which the jig omits the inclusion of a fourth passageway (e.g., jig 10'), step 314 can alternatively comprise advancing the third needle 210' through the opening created in the mandible such that the third needle 210' extends through the entire opening and through a second portion of the tongue of the patient, different from the first portion, with a portion of the device (e.g., first end 220') disposed outside of the opening and adjacent the chin and another portion of the device (e.g., tapered second end 222') disposed outside of the opening and adjacent the tongue. For example, the third needle 210' can be advanced such that it is advanced through one of the openings (e.g., right dorsal puncture site) of the transverse passageway created in step 310.

Another step 316 comprises passing the first needle through the transverse passageway in the tongue such that the distal end and the notch of the elongate shaft are disposed beyond one end of the passageway and outside of the tongue and a portion of the elongate shaft that is disposed proximal to the bend is disposed beyond another end of the passageway and outside of the tongue. Optionally, this step can be omitted in methods in which the first needle has not been removed from the first passageway after the first passageway is been created (e.g., first needle has not been removed after step 310).

Another step 318 comprises engaging a sling with the notch of the first needle that is disposed through the transverse passageway in the tongue such that the sling is releasably attached to the first needle. Any suitable sling can be used with the devices, methods, and kits described herein. Example slings are described in copending U.S. Nonprovisional application Ser. No. 13/550,065, filed Jul. 16, 2012. The entire contents of this application are hereby incorporated by reference into this disclosure by reference.

Another step 320 comprises pulling the first needle and the attached sling through the transverse passageway in the tongue until the sling is disposed in the transverse passageway with a portion of the sling extending beyond one end of the passageway and outside of the tongue and another portion of the sling extending beyond another end of the passageway and outside of the tongue. This step can be accomplished by applying a rotational force to the handle of the first needle such that the first needle rotates about the lengthwise axis the elongate shaft (e.g., counter-clockwise direction, clockwise direction).

Another step 322 comprises engaging a first portion of the sling, such as the first end of the sling, with the notch 228 of the tongue-adjacent end of the second needle 210 disposed in the first of the two openings in the mandible such that a pulling force applied to the second needle 210 will result in the first end of the sling being pulled along with the second needle 210 through the tongue and the first opening in the mandible.

Another step 324 comprises engaging a second portion of the sling, such as the second end of the sling, with the notch 228' tongue-adjacent end of the third needle 210' disposed in the second of the two openings in the mandible such that a pulling force applied to the third needle 210' will result in the second end of the sling being pulled along with the third needle 210' through the tongue and the second opening in the mandible.

Another step 326 comprises pulling the second needle 210 and third needle 210' and the first and second ends of the sling through the respective openings in the mandible until each end of the sling has exited the respective opening. It is considered advantageous to perform this step by pulling each of the needles simultaneously and at substantially the same rate with substantially the same force, but the needles can be pulled sequentially or with different rates and/or forces if considered desirable and/or necessary. Performance of this step results in each of the ends of the sling being pulled through one of the first and second openings in the tongue. In embodiments in which the jig omits the inclusion of a fourth passageway (e.g., jig 10'), step 326 can alternatively comprise pulling the second needle 210 and third needle 210' and the first and second ends of the sling through the opening in the mandible until each end of the sling has exited the opening.

Another step 328 comprises pulling the tongue toward the front of the mouth or mandible by pulling on one or both of the second needle 210 and third needle 210' and/or one or both of the first and second ends of the sling. An optional step comprises removing the sling from the second needle 210. Another optional step comprises removing the sling from the third needle 210'.

Another step 330 comprises securing the sling. This can be accomplished once a desired configuration of the tongue has been achieved and by securing the sling to itself, a tissue, or bone, such as the mandible, to support the tongue in the new position. For example, an optional step can comprise tying the first end of the sling with the second end of the sling to achieve securement of the sling in place. Another step can comprise sealing the openings in the mandible, such as with bone cement or other suitable composition and/or technique.

Another step 332 comprises closing the incision. This step can be accomplished using any suitable technique or tool (e.g., using sutures). Optionally, this step can be accomplished using a preserved cuff of gingiva to facilitate closure of the incision.

Figure 13:
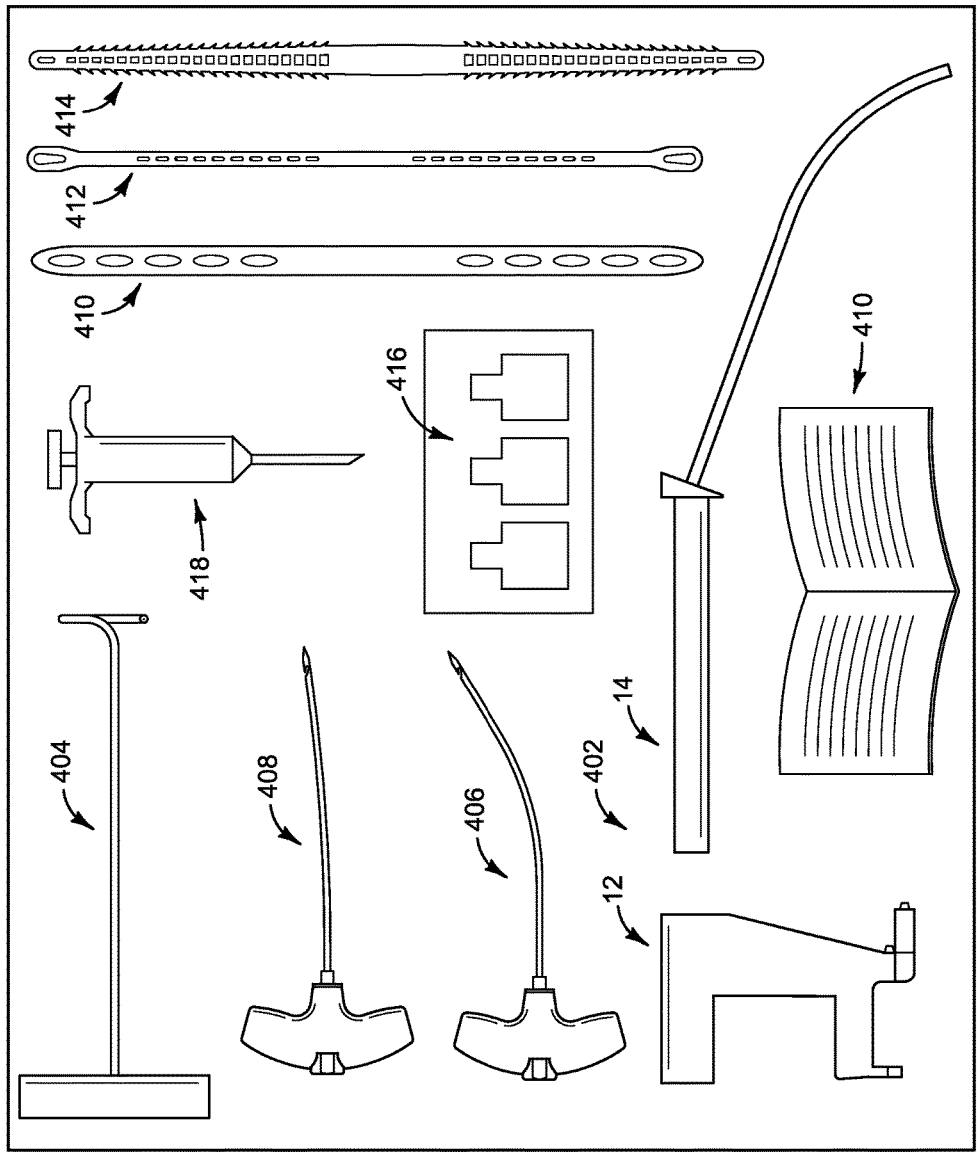
FIG. 13 illustrates a kit that includes a jig, a first needle, a second needle, and a third needle according to an embodiment.

FIG. 13 illustrates a kit 400 that comprises a jig 402 according to an embodiment, such as jig 10 (e.g., drill guide 12, tongue depressor 14); a first needle 404 according to an embodiment, such as first needle 110; a second needle 406 according to an embodiment, such as second needle 210; a third needle 408 according to an embodiment, such as third needle 210'; a first sling 410 according to an embodiment; a second sling 412 according to an embodiment; a third sling 414 according to an embodiment; a plurality of vials of bone cement 416; an injection device 418 to introduce the bone cement into an opening; and instructions for use 420.

Optionally a kit can include one or more placement rods that comprise an elongate shaft that has a first end and a second end and a length disposed between the first end and the second end. Each placement rod has a length that is equal to, substantially equal to, or greater than the combined length of the third passageway and the length of the first opening created in the mandible or the combined length of the fourth passageway and the length of the second opening created in the mandible. Optionally a kit can include one or more set screws that are adapted to be passed through an aperture defined by the drill guide. Optionally, a kit can include one or more drill bits (e.g., 3 millimeter drill bit, drill bit having an outside diameter greater than 3 millimeters) to create one or more openings in the mandible of the patient. Optionally, a kit can include a bone cement mixer.

While a single delivery system jig 402, a first needle 404, a second needle 406, a third needle 408, a first sling 410, a second sling 412, and a third sling 414, a plurality of vials of bone cement 416, and an injection device 418 have been illustrated in kit 400, any suitable type and/or number of jigs, needles, slings, vials of bone cement, and injection devices can be included in kit 400. Skilled artisans will be able to select a suitable number of jigs, needles, slings, vials of bone cement, and injection devices according to a particular embodiment based on various considerations, including the intended recipient of the kit. Example numbers of jigs, needles, slings, vials of bone cement, and injection devices considered suitable to include in a kit include, but are not limited to, one, at least one, two, a plurality, three, four and any other number considered suitable for a particular application. Example devices considered suitable to include in a kit include jig 10, jig 10', first needle 110, first needle 110', second needle 210, third needle 210', any suitable sling, any suitable delivery device, any suitable mixing device, and any other device considered suitable for a particular embodiment.

The foregoing detailed description refers to medical devices, kits containing the medical devices and other devices that facilitate their use, and methods of treatment based on use of the medical devices and includes the best mode for practicing the invention. The description and the appended drawings illustrating the described devices, methods, and kits are intended only to provide examples and not to limit the scope of the claims in any manner.

What is claimed is:

1. A jig for use on the mandible of a patient, the jig comprising:
    a drill guide having a proximal end, a distal end, and a body defining a first passageway, a second passageway, a third passageway, a fourth passageway, and a protuberance, the protuberance extending outward and away from the distal end of the drill guide; and
    a tongue depressor releasably attached to the drill guide, the tongue depressor having a proximal end, a distal end, and a body that defines a track and an elongate member, the track extending from the proximal end of the tongue depressor toward the distal end of the tongue depressor and having a first shaft and a second shaft, the first shaft adapted to be received by the first passageway of the drill guide and having a lengthwise axis, the second shaft adapted to be received by the second passageway of the drill guide and having a lengthwise axis, the elongate member extending from the track to the distal end of the tongue depressor and having a proximal end and a distal end, the body of the tongue depressor defining a curve between the proximal end and the distal end of the elongate member, a portion of the elongate member extending from the proximal adjacent the track disposed at an angle to a plane that contains the lengthwise axis of the first shaft and the lengthwise axis of the second shaft, the angle being between about 0 degrees and about 45 degrees.

2. The jig of claim 1, wherein the first passageway defined by the drill guide has a first length;
    wherein the first shaft of the track has a second length; and
    wherein the first length is less than the second length.

3. The jig of claim 1, wherein the second passageway defined by the drill guide has a first length;
    wherein the second shaft of the track has a second length; and
    wherein the first length is less than the second length.

4. The jig of claim 1, wherein the first passageway defined by the drill guide has a first length;
    wherein the third passageway defined by the drill guide has a second length; and
    wherein the first length is greater than the second length.

5. The jig of claim 1, wherein the first passageway defined by the drill guide has a first length;
    wherein the fourth passageway defined by the drill guide has a second length; and
    wherein the first length is greater than the second length.

6. The jig of claim 1, wherein the drill guide has a first length from the proximal end of the drill guide to the distal end of the drill guide;
    wherein the drill guide has a second length from the proximal end of the drill guide to the distal end of the drill guide; and
    wherein the second length is less than the first length.

7. The jig of claim 6, wherein the body of the drill guide defines a sloped surface on the distal end of the drill guide.

8. The jig of claim 1, wherein the body of the drill guide defines a second protuberance and a third protuberance, each of the second protuberance and third protuberance extending outward and away from the distal end of the drill guide.

9. The jig of claim 1, wherein the first passageway is disposed a first distance from the second passageway;
    wherein the third passageway is disposed a second distance from the fourth passageway; and
    wherein the first distance is greater than the second distance.

10. The jig of claim 1, wherein the first passageway has a first inside diameter;
    wherein the third passageway has a second inside diameter; and
    wherein the first inside diameter is greater than the second inside diameter.

11. The jig of claim 1, wherein the portion of the elongate member adjacent the track has a lengthwise axis; and
    wherein the curve extends from the portion of the elongate member adjacent the track and away from the lengthwise axis of the portion of the elongate member adjacent the track.

12. A jig for use on the mandible of a patient, the jig comprising:
    a drill guide having a proximal end, a distal end, and a body defining a first passageway, a second passageway, a third passageway, a fourth passageway, and a protuberance, the first passageway having a first length, the second passageway having a second length, the protuberance extending outward and away from the distal end of the drill guide; and
    a tongue depressor releasably attached to the drill guide, the tongue depressor having a proximal end, a distal end, and a body that defines a track and an elongate member, the track extending from the proximal end of the tongue depressor toward the distal end of the tongue depressor and having a first shaft and a second shaft, the first shaft adapted to be received by the first passageway of the drill guide and having a third length and a lengthwise axis, the second shaft adapted to be received by the second passageway of the drill guide and having a fourth length and a lengthwise axis, the elongate member extending from the track to the distal end of the tongue depressor and having a proximal end and a distal end, the body of the tongue depressor defining a curve between the proximal end and the distal end of the elongate member, a portion of the elongate member adjacent the track disposed at an angle to a plane that contains the lengthwise axis of the first shaft and the lengthwise axis of the second shaft, the angle being between about 0 degrees and about 45 degrees;

wherein the first length is less than the third length; and
wherein the second length is less than the fourth length.

13. The jig of claim 12, wherein the third passageway defined by the drill guide has a fifth length; and
wherein the first length of the first passageway is greater than the fifth length.

14. The jig of claim 12, wherein the fourth passageway defined by the drill guide has a fifth length; and
wherein the first length of the first passageway is greater than the fifth length.

15. The jig of claim 12, wherein the drill guide has a fifth length from the proximal end of the drill guide to the distal end of the drill guide;
wherein the drill guide has a sixth length from the proximal end of the drill guide to the distal end of the drill guide; and
wherein the sixth length is less than the fifth length.

16. The jig of claim 15, wherein the body of the drill guide defines a sloped surface on the distal end of the drill guide.

17. The jig of claim 12, wherein the body of the drill guide defines a second protuberance and a third protuberance, each of the second protuberance and third protuberance extending outward and away from the distal end of the drill guide.

18. The jig of claim 12, wherein the first passageway is disposed a first distance from the second passageway;
wherein the third passageway is disposed a second distance from the fourth passageway; and
wherein the first distance is greater than the second distance.

19. The jig of claim 12, wherein the first passageway has a first inside diameter;
wherein the third passageway has a second inside diameter; and
wherein the first inside diameter is greater than the second inside diameter.

20. A method of treating Obstructive Sleep Apnea in a patient, said method comprising the steps of:
placing a jig on the mandible of said patient, the jig comprising:
a drill guide having a proximal end, a distal end, and a body defining a first passageway, a second passageway, a third passageway, a fourth passageway, and a protuberance, the protuberance extending outward and away from the distal end of the drill guide; and
a tongue depressor releasably attached to the drill guide, the tongue depressor having a proximal end, a distal end, and a body that defines a track and an elongate member, the track extending from the proximal end of the tongue depressor toward the distal end of the tongue depressor and having a first shaft and a second shaft, the first shaft adapted to be received by the first passageway of the drill guide and having a lengthwise axis, the second shaft adapted to be received by the second passageway of the drill guide and having a lengthwise axis, the elongate member extending from the track to the distal end of the tongue depressor and having a proximal end and a distal end, the body of the tongue depressor defining a curve between the proximal end and the distal end of the elongate member, a portion of the elongate member adjacent the track disposed at an angle to a plane that contains the lengthwise axis of the first shaft and the lengthwise axis of the second shaft, the angle being between about 0 degrees and about 45 degrees;
creating a first opening in the mandible of said patient by passing a medical device through the third passageway defined by the drill guide;
creating a second opening in the mandible of said patient by passing a medical device through the third passageway defined by the drill guide;
creating a transverse passageway in the tongue of said patient;
pulling a sling having first and second ends through the transverse passageway using a first needle having an elongate shaft that defines a bend and a curve;
pulling the first end of the sling through the first opening in the mandible of said patient using a second needle having an elongate shaft and defining a curve;
pulling the second end of the sling through the second opening in the mandible of said patient using a third needle having an elongate shaft and defining a curve;
pulling the first and second ends of the sling away from the mandible of said patient to advance the tongue toward the front of the mandible of said patient; and
securing the sling to the mandible of said patient to support the tongue.

* * * * *

UNITED STATES PATENT AND TRADEMARK OFFICE
CERTIFICATE OF CORRECTION

PATENT NO. : 10,123,900 B2
APPLICATION NO. : 14/211704
DATED : November 13, 2018
INVENTOR(S) : Arun Mohan et al.

Page 1 of 1

It is certified that error appears in the above-identified patent and that said Letters Patent is hereby corrected as shown below:

In the Claims

Claim 1, at Column 19, Lines 53 through 57, reads "a portion of the elongate member extending from the proximal adjacent the track disposed at an angle to a plane that contains the lengthwise axis of the first shaft and the lengthwise axis of the second shaft".

Claim 1, at Column 19, Lines 53 through 57, should read --a portion of the elongate member adjacent the track disposed at an angle to a plane that contains the lengthwise axis of the first shaft and the lengthwise axis of the second shaft--.

Signed and Sealed this
Eighth Day of January, 2019

Andrei Iancu
*Director of the United States Patent and Trademark Office*